US006515161B1

(12) United States Patent
Kreutzer et al.

(10) Patent No.: US 6,515,161 B1
(45) Date of Patent: Feb. 4, 2003

(54) HYDROFORMYLATION PROCESS UTILIZING MULTIDENTATE PHOSPHITE LIGANDS

(75) Inventors: Kristina Ann Kreutzer, Wlimington, DE (US); Wilson Tam, Boothwyn, PA (US); John Ronald Boyles, Wilmington, DE (US); J Michael Garner, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/650,609

(22) Filed: Aug. 30, 2000

Related U.S. Application Data

(60) Provisional application No. 60/154,728, filed on Sep. 20, 1999.

(51) Int. Cl.$^7$ ............................................. C06C 255/00
(52) U.S. Cl. ..................... 558/353; 560/175; 568/454
(58) Field of Search ................... 558/353; 560/175; 568/454

(56) References Cited

U.S. PATENT DOCUMENTS

| | | |
|---|---|---|
| 3,496,215 A | 2/1970 | Drinkard et al. |
| 3,496,217 A | 2/1970 | Drinkard, Jr. et al. |
| 3,536,748 A | 10/1970 | Drinkard, Jr. et al. |
| 3,676,481 A | 7/1972 | Chia |
| 3,907,847 A | 9/1975 | Kestutis |
| 5,210,260 A | 5/1993 | Bohshar et al. |
| 5,235,113 A | 8/1993 | Sato et al. |
| 5,512,696 A | 4/1996 | Kreutzer et al. ............. 558/338 |
| 5,663,369 A | 9/1997 | Kreutzer et al. ............. 549/212 |
| 5,688,986 A | 11/1997 | Tam et al. ................... 558/338 |
| 5,723,641 A | 3/1998 | Tam et al. ..................... 556/13 |
| 5,821,378 A | 10/1998 | Foo et al. .................... 558/338 |
| 5,847,191 A | 12/1998 | Bunel et al. ................. 558/338 |
| 5,910,600 A | 6/1999 | Urata et al. .................. 558/162 |

FOREIGN PATENT DOCUMENTS

| | | |
|---|---|---|
| DE | 19717359 | 11/1997 |
| WO | WO95/14659 | 6/1995 |
| WO | WO95/30680 | 11/1995 |
| WO | WO96/16022 | 5/1996 |
| WO | WO96/22968 | 8/1996 |
| WO | WO 99/06357 | 2/1999 |
| WO | WO99/06359 | 2/1999 |

OTHER PUBLICATIONS

Donald L. Jameson, et al., Design and Synthesis of a Series of Facially Coordinating Tridentate Ligands, Tetrahedron Letters (1989) pp. 1609–1612, vol. 30, No. 13, Gettysburg, PA.

Gregory D. Cuny, et al., Practical, High–Yield, Regioselective, Rhodium–Catalyzed Hydroformylation of Functionalized a–Olefins, J.A. Chem. Soc. (1993) pp. 2066–2068, vol. 115.

Leonard E. Miller, et al., The Reactivity of the Methyl Group in 2–Methyl–3–nitronaphthalene, J. A. Chem. Soc. (1954) pp. 296–297, vol. 76.

Giovanni Casiraghi, et al., Uncatalyzed Phenol–Formaldehyde Reactions. A Convenient Synthesis of Substituted 2,2'Dihydroxy–diphenylmethanes, Synthesis (1981) pp. 143–146, vol. 2.

Warren W. Kaeding Oxidation of Phenols with Cupric Salts, Journal of Organic Chemistry, (1963), pp. 1063–1067, vol. 28.

T. Jongsma P. Kimes, et al., A New Type of Highly Active Polymer–Bound Rhodium Hydroformylation Catalyst, Polymer (1992) pp. 161–165, vol. 33.

Wei–Bo Wang, et al., An Efficient SbC13–Metal System for Allylation, Reduction and Acetalization of Aldehydes, Tetrahedron (1990) pp. 3315–3320, vol. 46, No. 9.

Martin Hovorka, et al., Highly Selective Oxidative Cross–Coupling of Substituted 2–Naphthols: A Convenient Approach to Unsymmetrical 1,1–Bimaphthalene–2,2'–Diols, Tetrahedron Letters (1990) pp. 413–416, vol. 31, No. 3.

B.F. Gisin, The Preparation of Merrifield–Resins Through Total Esterification With Cesium Salts, Helvetica Chimica Acta 1973) pp. 1476–1482, vol. 56, Fasc. 5.

Claire Le. Hetet, Synthesis of Functionalized y and o–Lactones via Polymer–Bound Epoxides, Tetrahedron Letters (1997) pp. 5153–5156, vol. 38, No. 29.

Achim Kless, The First Chiral Early–Late Heterobimetallic Complex–A Titanium(IV)–Palladium(II) Complex Based on Salenophos, Tetrahedron (1996) pp. 14599–14606, vol. 52, No. 46.

Anderson De Farias Dias, An Improved High Yield Synthesis of Dehydrodieugenol, Phytochemistry (1988) pp. 3008–3009, vol. 27, No. 9.

Martin Hovorka, et al. An Optimized Synthesis of Dimethyl 2,2'–Dihydroxy–1,1'–Binaphthalene–3,3'–Dicarboxylate and of Methyl 2,2'–Dihydroxy–1, 1'–Binaphthalene–3–Carboxylate, Organic Prep. and Proc. International (1991) pp. 200–203, vol. 23, No. 2.

John T. Pinhey, et al. The Thermal ortho–Substitution, Aust. J. Chem. (1988) pp. 69–80, vol. 41.

Fukiko Yamada, et al., Substituted Bisphenols as Antioxidants for Autoxidation of Tetralin, The Chemical Society of Japan—Bull. Chem. Soc. (1989) pp. 3603–3608, vol. 62.

*Primary Examiner*—Michael L. Shippen

(57) ABSTRACT

A hydroformylation process is disclosed which employs multidentate phosphite ligands in a catalyst composition. In particular, the ligands have heteroatom-containing substituents on the carbon attached to the ortho position of the terminal phenol group.

18 Claims, No Drawings

HYDROFORMYLATION PROCESS UTILIZING MULTIDENTATE PHOSPHITE LIGANDS

CROSS REFERENCE TO RELATED APPLICATION

This application claims the benefit of U.S. Provisional Application No. 60/154,728 filed Sep. 20, 1999.

FIELD OF THE INVENTION

The invention relates to a hydroformylation process using certain multidentate phosphite ligands. In particular, the ligands have heteroatom-containing substituents on the carbon attached to the ortho position of the terminal phenol group.

TECHNICAL BACKGROUND OF THE INVENTION

Phosphorus ligands are ubiquitous in catalysis and are used for a number of commercially important chemical transformations. Phosphorus ligands commonly encountered in catalysis include phosphines (A), and phosphites (B), shown below. In these representations, R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

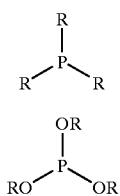

There are several industrially important catalytic processes employing phosphorus ligands. For example, U.S. Pat. No. 5,910,600 to Urata, et al. discloses that bisphosphite compounds can be used as a constituting element of a homogeneous metal catalyst for various reactions such as hydrogenation, hydroformylation, hydrocyanation, hydrocarboxylation, hydroamidation, hydroesterification and aldol condensation.

Some of these catalytic processes are used in the commercial production of polymers, solvents, plasticizers and other commodity chemicals. Consequently, due to the extremely large worldwide chemical commodity market, even small incremental advances in yield or selectivity in any of these commercially important reactions are highly desirable. Furthermore, the discovery of certain ligands that may be useful for applications across a range of these commercially important reactions is also highly desirable not only for the commercial benefit, but also to enable consolidation and focusing of research and development efforts to a particular group of compounds.

One industrially important catalytic reaction using phosphorus ligands of particular importance is olefin hydroformylation. For example, U.S. Pat. No. 5,235,113 to Sato, et al. discloses a hydroformylation process in which an organic bidentate ligand containing two phosphorus atoms linked with an organic dihydroxyl bridging group is used in a homogeneous hydroformylation catalyst system. Hydroformylation processes involving organic bidentate ligands containing two trivalent phosphorus atoms, in which the two phosphorous atoms are linked with a 2,2' dihydroxyl-1,1'-binaphthalene bridging group, are described in commonly assigned, copending application Ser. No. 60/087,151, filed May 29, 1998, and the patents and publications referenced therein.

Commonly assigned, published PCT Application W099/06357 discloses multidentate phosphite ligands with a structure having alkyl ether substituents on the carbon attached to the ortho position of the terminal phenol group for use in a liquid phase process for the hydrocyanation of diolefinic compounds.

It always remains desirable to provide even more effective, higher performing catalyst precursor compositions, catalytic compositions and catalytic processes to achieve full commercial potential for a desired reaction such as hydroformylation. The effectiveness and/or performance may be achieved in any or all of rapidity, selectivity, efficiency or stability. Other objects and advantages of the present invention will become apparent to those skilled in the art upon reference to the detailed description which hereinafter follows.

SUMMARY OF THE INVENTION

The invention provides for a hydroformylation process comprising reacting an acyclic, monoethylenically unsaturated compound with CO and $H_2$ in the presence of a catalyst precursor composition comprising a transition metal, and at least one multidentate phosphite ligand selected from the group represented by the following formulae I, I-A or I-B, in which all like reference characters have the same meaning, except as further explicitly limited.

The invention further provides for the hydroformylation of aromatic olefins comprising reacting an acyclic aromatic olefin compound with CO and $H_2$ in the presence of a catalyst precursor composition comprising a low-valent transition metal, and at least one multidentate phosphite ligand selected from the group represented by the following formulae I, I-A or I-B, in which all like reference characters have the same meaning, except as further explicitly limited.

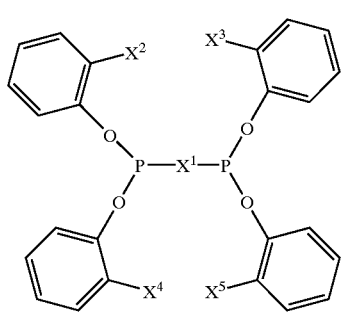

Formula I wherein $X^1$ is a bridging group and is selected from the group consisting of:

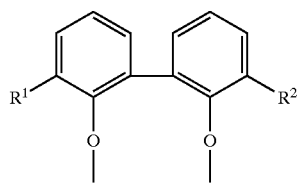

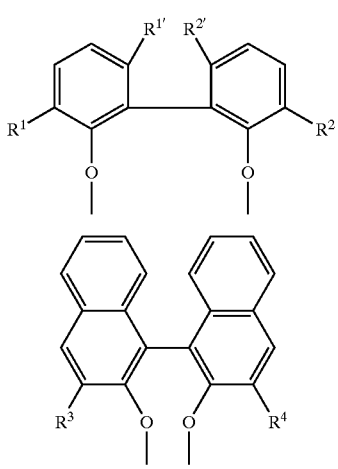

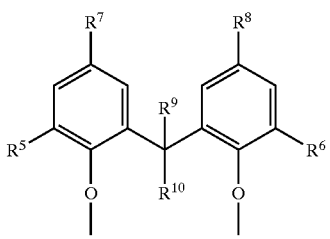

wherein $R^1$, $R^2$, $R^3$ $R^4$, $R^5$, $R^6$, $R^7$, $R^8$, $R^{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR_2^{12}$, acetal, ketal, dialkylamino, or diarylamino, —$OR^{11}$, —$CO_2R^{11}$, —$(CNR^{11})R^{11}$, —$(CNOR^{11})R^{11}$, wherein $R^{11}$ is $C_1$ to $C_{18}$ alkyl, aryl, or substituted aryl, —$C(O)R^{12}$, —$C(O)NR^{12}R^{13}$, —O—$C(O)R^{12}$, —$NR^{12}$—$C(O)R^{13}$, wherein $R^{12}$ and $R^{13}$ are independently selected from the group of H, $C_1$ to $C_{18}$ alkyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR^{11}$, —$CO_2R^{11}$, $RCNR^{11}$, or $RCNOR^{11}$, wherein $R^9$ and $R^{10}$ are independently selected from the group consisting of H, $C_1$ to $C_{18}$ alkyl, cycloalkyl, aryl, or substituted aryl;

wherein $X^2$ through $X^5$ are independently selected from the group consisting of:

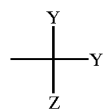

wherein Y is independently selected from the group consisting of H, aryl, $CR^{14}_3$, $(CR^{14}_2)n$—$OR^{14}$, $(CR^{14}_2)n$—$NR^{15}$, wherein $R^{14}$ is H, $C_1$–$C_{18}$ alkyl, cycloalkyl, or aryl, wherein $R^{15}$ is selected from the group consisting of H, alkyl, aryl, —$SO_2R^{11}$, —$SO_2NR^{12}_2$, —$COR^{16}$, wherein $R^{16}$ is H, $C_1$–$C_{18}$ alkyl, cycloalkyl, aryl or perfluoroalkyl;

and Z is selected from the group consisting of $(CR^{14}_2)n$—$OR^{14}$ wherein n=0–3.

Formula I-A

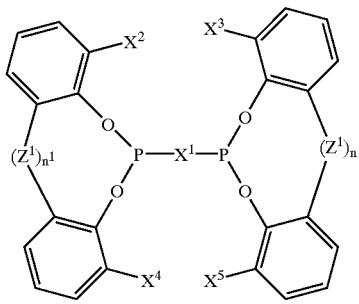

In other embodiments of the invention a ligand of the structure of Formula I-A may be substituted for the ligand of Formula I, and in those embodiments an aromatic ring carbon in the ortho position to an O bonded to a P may be bonded through $(Z^1)n^1$ to another aromatic ring carbon in the ortho position to the other O bonded to the P;

wherein $Z^1$ is independently

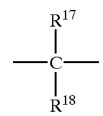

and each of $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1$=0 represents a bond replacing the two aromatic ring hydrogens.

Formula I-B

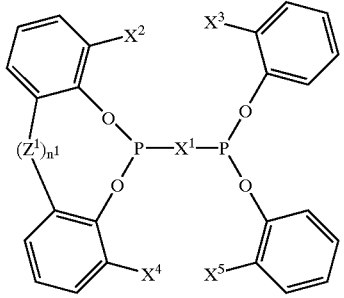

In other embodiments of the invention a ligand of the structure of Formula I-B may be substituted for the ligand of Formula I, and wherein an aromatic ring carbon in the ortho position to an O bonded to a P may be bonded through $(Z^1)n^1$ to another aromatic ring carbon in the ortho position to the other O bonded to the P;

wherein $Z^1$ is independently

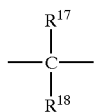

and each of $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1=0$ represents a bond replacing the two aromatic ring hydrogens.

Furthermore, in embodiments of the invention utilizing Formula I, Formula I-A or Formula I-B, either one of the Y's may be linked with Z to form a cyclic ether.

The invention further provides for a hydroformylation process comprising reacting an acyclic, monoethylenically unsaturated compound with CO and $H_2$ in the presence of a catalyst precursor composition comprising a transition metal, and at least one multidentate phosphite ligand selected from the group represented by the following formulae II, II-A or II-B, in which all like reference characters have the same meaning, except as further explicitly limited.

The invention further provides for the hydroformylation of aromatic olefins comprising reacting an acyclic aromatic olefin compound with CO and $H_2$ in the presence of a catalyst precursor composition comprising a low-valent transition metal, and at least one multidentate phosphite ligand selected from the group represented by the following formulae II, II-A or II-B, in which all like reference characters have the same meaning, except as further explicitly limited.

Formula II

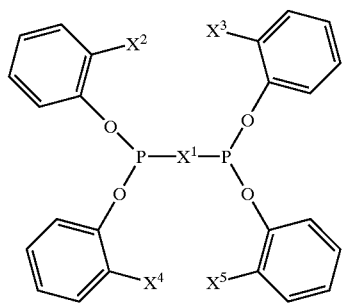

wherein $X^1$ is a divalent bridging group and is selected from the group consisting of:

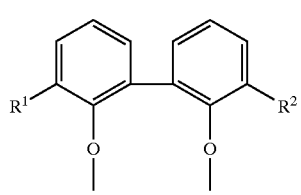

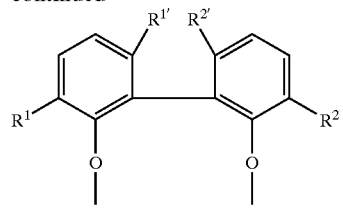

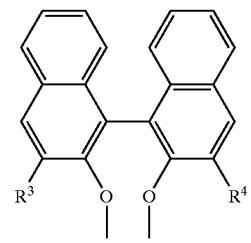

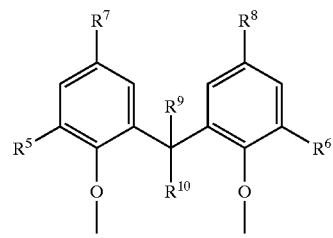

wherein $R^1$, $R^2$, $R^3$, $R^4$, $R^5$, $R^6$, $R^7$, $R^8$, $R^{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR_2^{12}$, acetal, ketal, dialkylamino, or diarylamino, —$OR^{11}$, —$CO_2R^{11}$, —$(CNR^{11})R^{11}$, —$(CNOR^{11})R^{11}$, wherein $R^{11}$ is $C_1$ to $C_{18}$ alkyl, cycloalkyl, aryl, or substituted aryl, —$C(O)R^{12}$, —$C(O)NR^{12}R^{13}$, —O—$C(O)R^{12}$, —$NR^{12}$—$C(O)R^{13}$, wherein $R^{12}$ and $R^{13}$ are independently selected from the group of H, $C_1$ to $C_{18}$ alkyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR^{11}$, —$CO_2R^{11}$, $RCNR^{11}$, or $RCNOR^{11}$, wherein $R^9$ and $R^{10}$ are independently selected from the group consisting of H, $C_1$ to $C_{18}$ alkyl, cycloalkyl, aryl, or substituted aryl, wherein $X^2$ through $X^5$ are independently selected from the group consisting of:

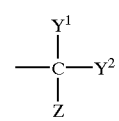

$Y^1$ is independently selected from the group consisting of H, aryl, $CR^{14}_3$, wherein $R^{14}$ is H, $C_1$–$C_{18}$ alkyl, cycloalkyl, or aryl, $(CR^{14}_2)n$—$OR^{14}$, $(CR^{14}_2)n$—

NR$^{15}$ wherein n is a number between 0 and 3, wherein R$^{15}$ is selected from the group consisting of H, alkyl, cycloalkyl, aryl, —SO$_2$R$^{11}$, —SO$_2$NR$^{12}{}_2$, —COR$^{16}$ wherein R$^{16}$ is H, C$_1$-C$_{18}$ alkyl, cycloalkyl, aryl, or perfluoroalkyl;

Y$^2$ is independently selected from the group consisting of aryl, CR$^{14}{}_3$, wherein R$^{14}$ is H, C$_1$-C$_{18}$ alkyl, cycloalkyl, or aryl, (CR$^{14}{}_2$)n—OR$^{14}$, (CR$^{14}{}_2$)n—NR$^{15}$ wherein n is a number between 0 and 3, wherein R$^{15}$ is selected from the group consisting of H, alkyl, cycloalkyl, aryl, —SO$_2$R$^{11}$, —SO$_2$NR$^{12}{}_2$, —COR$^{16}$ wherein R$^{16}$ is H, C$_1$-C$_{18}$ alkyl, cycloalkyl, aryl, or perfluoroalkyl;

Z is selected from the group consisting of (CR$^{14}{}_2$)$_n$—OR$^{14}$ wherein n=0–3.

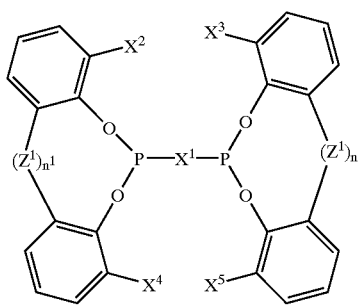

Formula II-A

In other embodiments of the invention a ligand of the structure of Formula II-A may be substituted for the ligand of Formula II, and wherein an aromatic ring carbon in the ortho position to an O bonded to a P may be bonded through (Z$^1$)n$^1$ to another aromatic ring carbon in the ortho position to the other O bonded to the P;

wherein Z$^1$ is independently

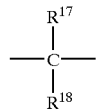

and each R$^{17}$ and R$^{18}$ are independently selected from the group consisting of H, C$_1$ to C$_{18}$ alkyl, cycloalkyl, aryl, or substituted aryl, n$^1$ is either one or zero; and wherein it is understood that n$^1$=0 represents a bond replacing the two aromatic ring hydrogens.

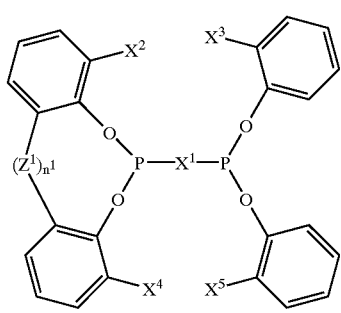

Formula II-B

In other embodiments of the invention a ligand of the structure of Formula II-B may be substituted for the ligand of Formula II, and an aromatic ring carbon in the ortho position to an O bonded to a P may be bonded through (Z$^1$)n$^1$ to another aromatic ring carbon in the ortho position to the other O bonded to the P;

wherein Z$^1$ is independently

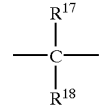

and each R$^{17}$ and R$^{18}$ are independently selected from the group consisting of H, C$_1$ to C$_{18}$ alkyl, cycloalkyl, aryl, or substituted aryl, n$^1$ is either one or zero; and wherein it is understood that n$^1$=0 represents a bond replacing the two aromatic ring hydrogens.

Furthermore, in embodiments of the invention utilizing Formula II, Formula II-A or Formula II-B, either Y$^1$ or Y$^2$ may be linked with Z to form a cyclic ether.

DETAILED DESCRIPTION OF THE PREFERRED EMBODIMENTS

The invention provides for an improved hydroformylation process which employs certain multidentate phosphite ligands. The catalyst compositions useful in the process of the invention are comprised of a multidentate phosphite ligand and a transition metal.

The divalent bridging compounds used in the ligands described in Formulae I, I-A, I-B, II, II-A, and II-B may be prepared by a variety of methods known in the art. For example, dimethyl 2,2'-dihydroxyl-1,1'-binaphthalene-3,3'-dicarboxylate can be prepared according to *J. Am. Chem. Soc.*, 1954, 76, 296 or in *Tetrahedron Lett.*, 1990, 413 and *Org. Proc. Prep. International*, 1991, 23, 200; 2,2'-ethylidenebis(4,6-dimethylphenol) can be prepared according to *Bull. Chem. Soc,. Japn.*, 1989, 62, 3603; 3,3',5,5'-tetramethyl-2,2'-biphenol can be prepared according to *J. Org. Chem.*, 1963, 28, 1063; 2,2'-dihydroxy-3,3'-dimethoxy-5,5'-dimethyl-1,1'-biphenylene can be prepared according to *Phytochemistry*, 1988, 27, 3008; and 3,3'-dimethyl-2,2'-dihydroxydiphenylmethane can be prepared according to *Synthesis*, 1981, 2, 143. 3,3',5,5',6,6'-Hexamethyl-2,2'-biphenol can be prepared according to JP 85-216749.

Acetal substituted salicylaldehydes can be prepared by those skilled in the art. For example, an acetal can be prepared by refluxing a glycol with salicylaldehyde in the presence of oxalic acid catalyst. For references for preparing acetals by the acid catalyzed reaction of an aldehyde and an alcohol, see *Tetrahedron*, 1996, 14599; *Tet. Lett.*, 1989, 1609; *Tetrahedron*, 1990, 3315. Cyclic ether substituted phenols can be prepared as described in *Aust. J. Chem.* 1988, 41, 69–80.

Phosphorochloridite may be prepared by a variety of methods known in the art, for example, see descriptions in *Polymer*, 1992, 33, 161; *Inorganic Synthesis*, 1966, 8, 68; U.S. Pat. No. 5,210,260; *Z. Anorg. Allg. Chem.*, 1986, 535, 221. With ortho-substituted phenols, phosphorochloridites can be prepared in situ from PCl$_3$ and the phenol. Also, phosphorochloridites of 1-naphthols can be prepared in situ from PCl$_3$ and 1-naphthols in the presence of a base like triethylamine. Another process for preparing the phosphochlorodite comprises treatment of N,N-dialkyl diarylphosphoramidite with HCl. ClP(OMe)$_2$ has been prepared in this manner, see *Z. Naturforsch*, 1972, 27B, 1429. Phosphorochloridites derived from substituted phenols have been prepared using this procedure as described in commonly assigned U.S. Pat. No. 5,821,378.

By contacting the thus obtained $(OAr)_2PCl$, wherein Ar is a substituted aryl, with a divalent bridging compound, for example by the method described in U.S. Pat. No. 5,235,113, a bidentate phosphite ligand is obtained which can be used in the process according to the invention.

Bis(phosphite)ligands supported on polymer resins such as Merrifield's resin can be prepared by similar methods, such as those described in Hetet, C. L., David, M., Carreaux, F., Carboni, B. and Sauleau, A., *Tetrahedron Lett.*, 1997, 38, 5153–5156, and Gisin, B. F. *Helv. Chim. Acta* 1973, 56, 1476–1482.

The transition metal may be any transition metal capable of carrying out catalytic transformations and may additionally contain labile ligands which are either displaced during the catalytic reaction, or take an active part in the catalytic transformation. Any of the transition metals may be considered in this regard. The preferred metals are those comprising group VIII of the Periodic Table. The preferred metals for hydroformylation are rhodium, cobalt, iridium, ruthenium, palladium and platinum.

Group VIII compounds suitable for hydroformylation, can be prepared or generated according to techniques well known in the art, as described, for example, WO 95 30680, U.S. Pat. No. 3,907,847, and *J. Amer. Chem. Soc.*, 1993, 115, 2066. Examples of suitable Group VIII metals are ruthenium, rhodium, and iridium. Suitable Group VIII metal compounds are hydrides, halides, organic acid salts, acetylacetonates, inorganic acid salts, oxides, carbonyl compounds and amine compounds of these metals. Examples of suitable Group VIII metal compounds are, for example, $Ru_3(CO)_{12}$, $Ru(NO_3)_2$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The Group VIII metal is preferably rhodium. Rhodium compounds that contain ligands which can be displaced by the multidentate phosphites are a preferred source of rhodium. Examples of such preferred rhodium compounds are $Rh(CO)_2$ (acetylacetonate), $Rh(CO)_2(C_4H_9COCHCO-t-C_4H_9)$, $Rh_2O_3$, $Rh_4(CO)_{12}$, $Rh6(CO)_{16}$, $Rh(O_2CCH_3)_2$, and $Rh(2$-ethylhexanoate). Rhodium supported on carbon may also be used in this respect.

DESCRIPTION OF SPECIFIC HYDROFORMYLATION PROCESSES—HYDROFORMYLATION OF MONOOLEFINIC COMPOUNDS

The present invention also provides a process for hydroformylation, comprising reacting a monoethylenically unsaturated compound with a source of CO and $H_2$ in the presence of a catalyst precursor composition comprising a transition metal selected from the group of Co, Rh, Ru, Ir, Pd, and Pt, and at least one multidentate phosphite ligand selected from the group represented by Formula I, I-A, I-B, II, II-A, or II-B as described above.

Representative ethylenically unsaturated compounds which are useful in the process of this invention are shown in Formulae III, V or VII, and the corresponding terminal aldehyde compounds produced are illustrated by Formulae IV, VI or VIII, respectively, wherein like reference characters have same meaning.

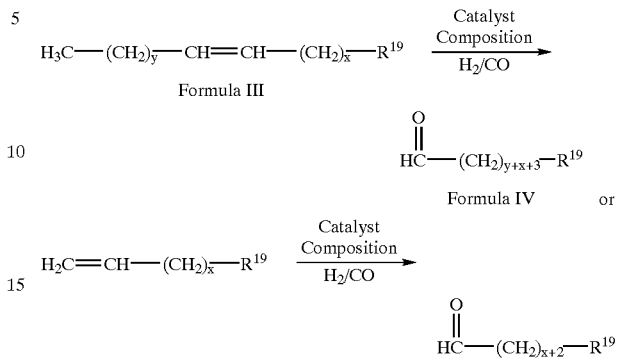

Formula III

Formula IV or wherein
$R^{19}$ is H, CN, $CO_2R^{20}$, or perfluoroalkyl;
y is an integer of 0 to 12;
x is an integer of 0 to 12 when $R^{19}$ is H, CHO, $CO_2R^{20}$ or perfluoroalkyl;
x is an integer of 1 to 12 when $R^{19}$ is CN; and
$R^{20}$ is $C_1$ to $C_{12}$ alkyl, or aryl.

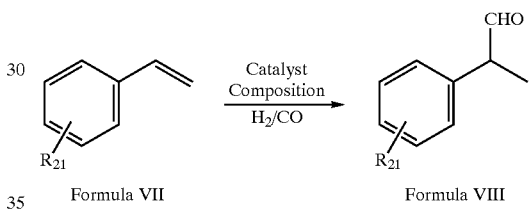

Formula VII                Formula VIII $R^{21}$ is an alkyl, aryl, aralkyl, alkaryl, or fused aromatic group of up to 20 carbon atoms; $R^{21}$ may further be branched or linear; $R^{21}$ may also contain heteroatoms such as O, N, and F.

The nonconjugated, aliphatic, monoolefinically unsaturated starting materials useful in this invention include unsaturated organic compounds containing from 2 to approximately 30 carbon atoms. Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, 1-butene, 2-pentene, 2-hexene, etc.; nonconjugated diethylenically unsaturated compounds such as allene; ethylenically unsaturated compounds having perfluoroalkyl substituents such as, for example, $C_zF_{2z+1}$, where z is an integer of up to 20; and substituted compounds such as allyl alcohol, 3-pentenenitrile, 4-pentenenitrile, methyl-3-pentenoate, methyl-4-pentenoate, 3-pentenal, 4-pentenal, and functional derivatives, such as acetals, imines, and hydrazones derived from 3- or 4-pentenal;. As used herein, the term "pentenenitrile" is intended to be identical with "cyanobutene". The monoolefins propylene, 1-butene, 2-butene, 3-pentenenitrile, and 4-pentenenitrile are especially preferred. As a practical matter, when the nonconjugated aliphatic monoethylenically unsaturated compounds are used in accordance with this invention, up to about 10% by weight of the monoethylenically unsaturated compound may be present in the form of a conjugated isomer, which itself may undergo hydroformylation.

Preferred are nonconjugated linear alkenes, nonconjugated linear alkenenitriles, nonconjugated alkyl pentenoates, nonconjugated pentenals, acetal derivatives of pentenals, and perfluoroalkyl ethylenes. Most preferred substrates include methyl-3-pentenoate, 3-pentenal (3-pentenealdehyde), 3- and 4-pentenenitrile and $C_zF_{2z+1}CH=CH_2$ (where z is 1 to 12).

The preferred products are terminal alkanealdehydes, linear aliphatic aldehyde nitriles, and 3-(perfluoroalkyl) propionaldehyde. Most preferred products are n-butyraldehyde, 2-phenylpropionaldehyde, and 5-cyanovaleraldehyde.

The reaction conditions of the hydroformylation process according to this invention are in general the same as used in a conventional process, described, for example, in U.S. Pat. No. 4,769,498, which is incorporated herein by reference and will be dependent on the particular starting ethylenically unsaturated organic compound. For example, the temperature can be from room temperature to 200° C., preferably from 50–120° C. The pressure may vary from atmospheric pressure to 20 MPa, preferably from 0.15 to 10 MPa and more preferably from 0.2 to 1 MPa. The pressure is, as a rule, equal to the combined hydrogen and carbon monoxide partial pressure. Extra inert gases may however be present. The molar ratio of hydrogen to carbon monoxide is generally between 10 to 1 and 1 to 10, preferably between 6 to 1 and most preferably 1 to 2.

The amount of rhodium compound is not specially limited, but is optionally selected so that favorable results can be obtained with respect to catalyst activity and economy. In general, the concentration of rhodium in the reaction medium is between 10 and 10,000 ppm and more preferably between 50–500 ppm, calculated as the free metal.

The molar ratio of multidentate phosphorus ligand to rhodium is not specially limited, but is optionally selected so that favorable results can be obtained with respect to catalyst activity, aldehyde selectivity, and process economy. This ratio generally is from about 0.5 to 100 and preferably from 1 to 10 (moles of ligand to moles of metal).

The choice of solvent is not critical provided the solvent is not detrimental to catalyst, reactant and product. The solvent may be a mixture of reactants, such as the starting unsaturated compound, the aldehyde product and/or by-products. Suitable solvents include saturated hydrocarbons such as kerosene, mineral oil or cyclohexane, ethers such as diphenyl ether, tetrahydrofuran or a polyglycol, ketones such as methyl ethyl ketone and cyclohexanone, nitrites such as methylglutaronitrile, valeronitrile, and benzonitrile, aromatics such as toluene, benzene and xylene, esters such as methyl valerate and caprolactone, dimethylformamide, and sulfones such as tetramethylenesulfone. The reaction may also be conducted with reactants and products in the gas phase.

Preferably, when a liquid reaction medium is used, the reaction mixture is agitated, such as by stirring or shaking.

Other catalysts useful in the practice of the present invention consist of the class of polymer-supported bis (phosphorus) ligands in combination with transition metal compounds, the metals of which are, for example, rhodium, ruthenium, cobalt, palladium or platinum. Alternatively, useful catalysts can be prepared from a combination of bis(phosphorus) ligand and a suitable transition metal complex, such as Rh(acetonylacetonate)(CO)$_2$ or Rh$_4$(CO)$_{12}$, dispersed on a suitable support, such as silica, alumina, carbon or a polymeric material.

The hydroformylation process according to the invention can be performed as described below:

The preferred temperature range is from about 50° C. to about 180° C., most preferably from about 90° C. to 110° C. The temperature must be chosen so as to maintain all of the reactants and products in the vapor phase, but low enough to prevent deterioration of the catalyst. The particular preferred temperature depends to some extent on the catalyst being used, the olefinic compound being used, and the desired reaction rate. The operating pressure is not particularly critical and can conveniently from about 1–10 atmospheres (101.3 to 1013 kPa). The pressure and temperature combination must be chosen so as to maintain reactants and products in the vapor phase.

The invention will now be illustrated by the following non-limiting examples of certain embodiments thereof, wherein all parts, proportions, and percentages are by weight, unless otherwise indicated.

The following definitions are applicable wherever the defined terms appear in this specification:

The term "hydrocarbyl" designates a hydrocarbon molecule from which one hydrogen atom has been removed. Such molecules can contain single, double or triple bonds.
M3P: methyl 3-pentenoate
COD: 1,5-cyclooctadiene
Et$_3$N: triethylamine
PCl$_3$: phosphorus trichloride
THF: tetrahydrofuran
3PN; 3-pentenenitrile
2PN: 2-pentenenitrile
4PN: 4-pentenenitrile
2M3: 2-methyl-3-butenenitrile
VN: valeronitrile
3FVN: 3-formylvaleronitrile
4FVN: 4-formylvaleronitrile
5FVN: 5-formylvaleronitrile
BD: 1,3-butadiene
c=cis
t=trans
L/M=ligand/metal An example of the protocol used to calculate conversion, linearity, and selectivity for a hydroformylation reaction follows:.
Total=c2PN+VN+t2PN+t3PN+4PN+c3PN+4FVN+3FVN+5FVN
Products=c2PN+VN+t2PN+4FVN+3FVN+5FVN
Accounting=Total/amount 3PN added initially
Conversion=Products/Total
Linearity=5FVN/(5FVN+4FVN+3FVN)
Selectivity=5FVN/Products

EXAMPLE 1

Synthesis of Acetal A

Salicylaldehyde (24.4 g, 200 mmol), ethylene glycol (31 g, 500 mmol), oxalic acid (1 g, 11 mmol), and toluene (150 mL) were combined and heated to reflux for 3 days in an apparatus equipped with a condenser and a Dean-Stark trap. After cooling, the solution was washed with NaHCO$_3$ and distilled water. The solution was dried over MgSO$_4$, and the solvent was evaporated to give 26 g of an off white solid. It was crystallized from hexane.

EXAMPLE 2

Synthesis of Acetal B

Salicylaldehyde (244 g, 2.0 mol), 1,3-propanediol (228 g, 3.0 mol), and oxalic acid (4.5 g, 0.05 mol) were added to 400 mL toluene and heated to reflux for 8 hours in an apparatus equipped with a condenser and a Dean-Stark trap. After cooling, the solution was washed with NaHCO$_3$ and distilled water, and the solution was dried over MgSO$_4$. The product precipitated when the solvent was being evaporated. The solid was collected and dissolved in hot hexane. The solution was filtered through Celite® (a filter aid manufactured by Johns Manville Corp.), and the product was crystallized to give 108 g of an off-white solid.

EXAMPLE 3

Synthesis of Acetal C

Salicylaldehyde (24 g, 0.2 mol), neopentyl glycol (20.9 g, 0.2 mol), oxalic acid (1 g, 11 mmol), and toluene (150 mL) were combined and heated to reflux for 2 days in an apparatus equipped with a condenser and a Dean-Stark trap. After cooling, the solution was washed with NaHCO$_3$ and distilled water. The solution was dried over MgSO$_4$, and the solvent was evaporated to give 39 g of a white solid, which was crystallized from hexane.

EXAMPLE 4

Synthesis of Acetal D

Salicylaldehyde (12.2 g, 0.1 mol) and trimethylorthoformate (10.6 g, 0.1 mol) were dissolved in dry MeOH (40 mL), and H$_2$SO$_4$ (0.25 g) was added. The reaction was stirred for 2 days under nitrogen at room temperature. The reaction was quenched by adding solid NaHCO$_3$ followed by Na$_2$CO$_3$ until the mixture became pH 9 or higher. The product was vacuum distilled (86.5–88° C., 2 torr), and 3.98 g of material was collected.

EXAMPLE 5

Synthesis of Amino-Acetal E

Salicylaldehyde (6.11 g, 0.05 mol), 2-anilinoethanol (8.23 g, 0.06 mol), and oxalic acid (0.45 g, 5 mmol) were dissolved in toluene (50 mL) and heated to reflux overnight in an apparatus equipped with a condenser and a Dean-Stark trap. After cooling, the solution was washed with aqueous NaHCO$_3$, distilled water, and the toluene solution was dried over MgSO$_4$. After filtration, hexane was added until the product began to precipitate. 5.89 g of solid was collected.

EXAMPLE 6

Synthesis of Acetal F

A 300 mL flask was charged with 14.929 g of 5-chlorosalicylaldehyde, 12.409 g of pinacol and 0.300 g of oxalic acid and 150 mL of toluene. The flask was connected to a Dean-Starke trap and the mixture refluxed overnight. The mixture was washed with aqueous sodium bicarbonate and the organic layer was dried over magnesium sulfate. The solvent was removed by rotary evaporation. A yellow solid was obtained which was recrystallized from hot hexane. The solid was washed with acetonitrile to give 7.118 g of white solid. $^1$H NMR (500 MHz, C$_6$D$_6$, δ): 7.9 (s, 1H), 7.17 (d, 2.6Hz, 1H), 7.08 (dd, J=2.6, 8.7 Hz, 1H), 6.73 (d, J=8.7Hz, 1H), 6.02 (s, 1H), 1.26 (s, 6H0, 1.18 (s, 6H).

EXAMPLE 7

Synthesis of Acetal G

A flask was charged with 18 g of 5-chlorosalicylaldehyde, 13 g of 1,3-propanediol and 2 g of oxalic acid and 200 mL of toluene. The flask was connected to a Dean-Stark trap and the mixture refluxed for 12 hours. The mixture was washed with water and aqueous sodium bicarbonate. The organic layer was dried over magnesium sulfate and the solvent removed by rotary evaporation. A light brown oil was obtained (22.3g) which solidified upon standing. $^1$H NMR (500 MHz, C$_6$D$_6$, δ): 7.7 (s, 1H), 6.96 (d, 2.6Hz, 1H), 6.72 (dd, J=2.6, 8.7 Hz, 1H), 6.49 (d, J=8.7Hz, 1H), 4.87(s, 1H), 3.37 (m, 2H), 2.99 (m, 2H), 1.37 (m, 1H), 0.35 (m, 1H).

EXAMPLE 8

Synthesis of Acetal H

Salicylaldehyde (24 g, 0.2 mol), 2-methyl-1,3-propanediol (18.0 g, 0.2 mol), oxalic acid (2.0 g), and toluene (250 mL) were combined and heated to reflux for 2 days in an apparatus equipped with a condenser and a Dean-Stark trap. After cooling, the solution was washed with NaHCO$_3$ (2×30 mL) and distilled water (30 mL). The solution was dried over MgSO$_4$, and the solvent was evaporated to give 39 g of a white solid, which was crystallized from hexane.

EXAMPLE 9

Synthesis of Ligand A

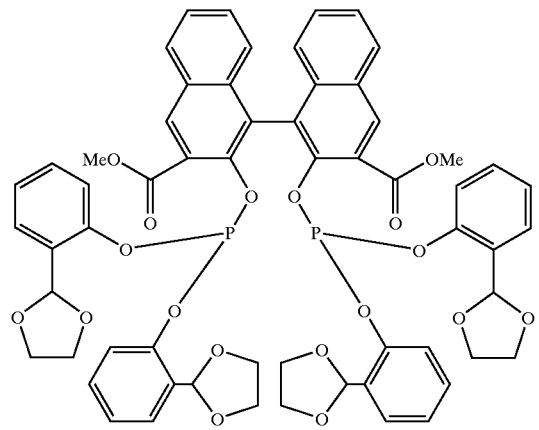

Acetal A (1.33 g, 8.0 mmol) and PCl$_3$ (0.55 g, 4 mmol) were dissolved in toluene (40 mL) and the solution was cooled to −40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.4 g, 4.0 mmol) and dimethyl 2,2'-dihydroxy-1,1'-binaphthalene-3,3'-dicarboxylate (0.8 g, 2.0 mmol) in toluene (15 mL) was added to the phosphorochloridite solution, and the mixture was stirred for 2 hours. The solution was filtered through Celite®, and the solvent was removed to give 2.0 g of product. $^{31}$P NMR (C$_6$D$_6$): δ 132.6, other peaks at 146.3, 130.3, 130.7 ppm.

EXAMPLE 10

Synthesis of Ligand B

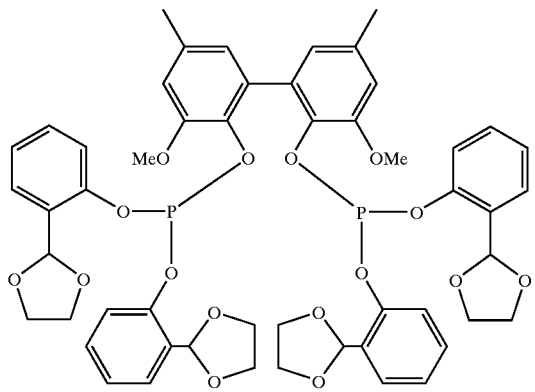

Acetal A (1.33 g, 8.0 mmol) and PCl₃ (0.55 g, 4 mmol) were dissolved in toluene (40 mL) and the solution was cooled to −40° C. Et₃N (1.0 g, 10.0 mmol) in toluene (15 mL) was added dropwise with stirring. The reaction was allowed to slowly warm to room temperature then stirred overnight. A mixture of Et₃N (0.4 g, 4.0 mmol) and 3,3'-dimethoxy-5,5'-dimethyl-2,2'-biphenol (0.55 g, 2.0 mmol) in toluene (15 mL) was added to the phosphorochloridite solution, and the mixture was stirred for 2 hours. The solution was filtered through Celite®, and the solvent was evaporated to give 1.8 g of product. $^{31}$P NMR (C₆D₆): δ 134.9, minor peaks at 145.4, 132.3 ppm.

EXAMPLE 11

Synthesis of Ligand C

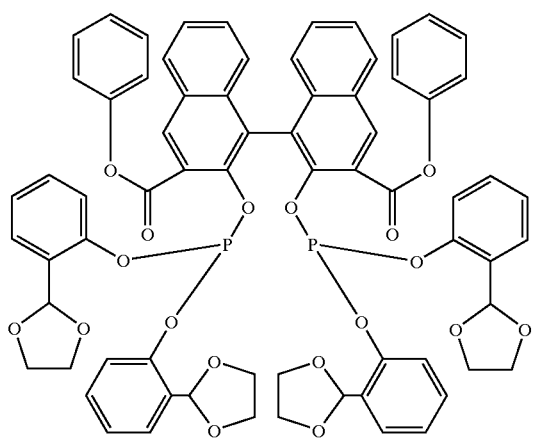

Acetal A (1.33 g, 8.0 mmol) and PCl₃ (0.55 g, 4 mmol) were dissolved in toluene (40 mL) and the solution was cooled to −40° C. Et₃N (1.0 g, 10.0 mmol) in toluene (15 mL) was added dropwise with stirring. The reaction was allowed to slowly warm to room temperature then stirred overnight. A mixture of Et₃N (0.4 g, 4.0 mmol) and diphenyl 2,2'-dihydroxy-1,1'-binaphthalene-3,3'-dicarboxylate (1.05 g, 2.0 mmol) in toluene (15 mL) was added to the phosphorochloridite solution, and the mixture was stirred for 2 hours. The solution was filtered through Celite®, and the solvent was removed to give 2.2 g of product. $^{31}$P NMR (C₆D₆): δ 130.2, minor peaks at 146.8, 131.4 ppm.

EXAMPLE 12

Synthesis of Ligand D

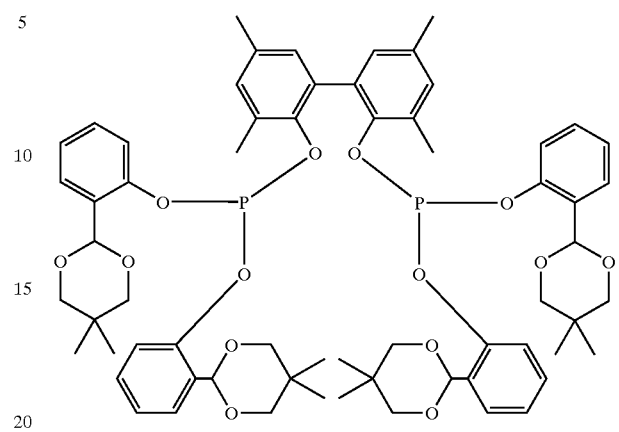

Acetal C (1.67 g, 8.0 mmol) and PCl₃ (0.55 g, 4 mmol) were dissolved in toluene (40 mL) and the solution was cooled to −40° C. Et₃N (1.0 g, 10.0 mmol) in toluene (15 mL) was added dropwise with stirring. The reaction was allowed to slowly warm to room temperature then stirred overnight. A mixture of Et₃N (0.4 g, 4.0 mmol) and 3,3',5,5'-tetramethyl-2,2'-biphenol (0.48 g, 2.0 mmol) in toluene (15 mL) was added to the phosphorochloridite solution, and the mixture was stirred for 2 hours. The solution was filtered through Celite®, and the solvent was evaporated to give 1.3 g of white sticky solid. $^{31}$p NMR (C₆D₆): δ 135.2, other peaks at 142.7, 134.5 ppm.

EXAMPLE 13

Synthesis of Ligand E

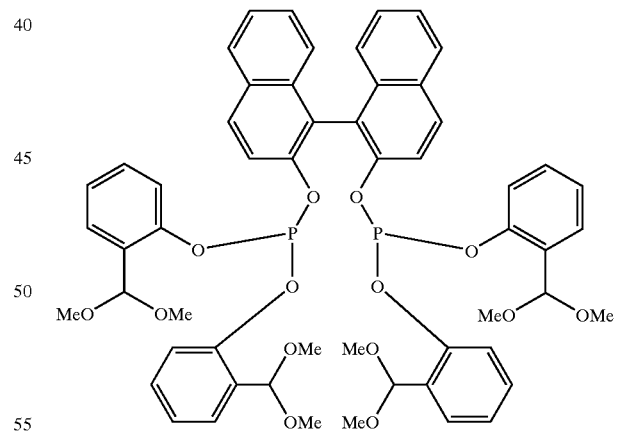

Acetal D (336 mg, 2.0 mmol) and Et₃N (1.0 g, 10.0 mmol) were dissolved in toluene (5 mL) and the solution was added dropwise to a stirred, −20° C. solution of PCl₃ (137 mg, 1.0 mmol) in toluene (2 mL). The reaction was stirred for 20 min, and then a mixture of 2,2'-binaphthol (143 mg, 0.5 mmol) and Et₃N (0.4 g, 4.0 mmol) in toluene (3 mL) was added to the phosphorochloridite solution, and the mixture was stirred 1 hour. The solution was filtered and the solvent was evaporated to give 0.57 g of product. $^{31}$P NMR (C₆D₆): δ 131.7, minor peaks at 146, 130.1 ppm.

EXAMPLE 14

Synthesis of Ligand F

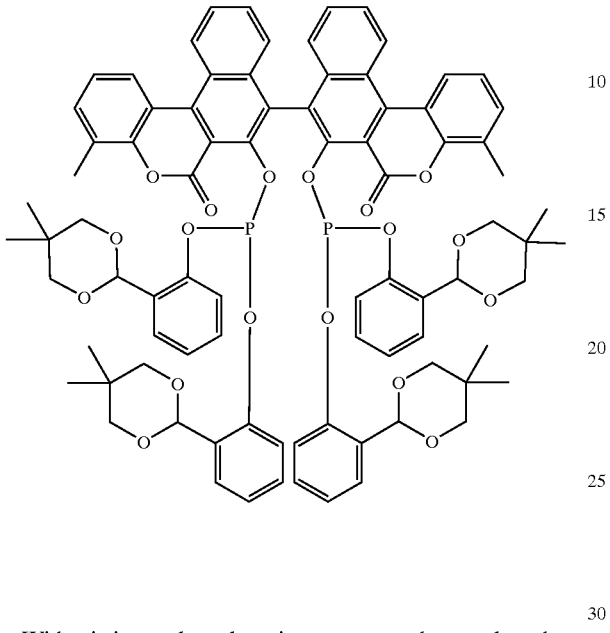

With stirring under a dry, nitrogen atmosphere, a dry ether solution (50 mL) of Acetal C was added dropwise over a 20 minute period to N,N-diethylphosphoramidous dichloride (3.36 gm, 19.3 mmol) and dry triethylamine (4.88 gm, 48.3 mmol) dissolved in 150 mL of dry ether. After stirring overnight, the triethylammonium chloride solids were vacuum filtered and washed with dry ether (3×15 mL). The combined ether filtrates were evaporated to yield the desired phosphoramidite, $[2-[5,5-(CH_3)_2-1,3-C_3H_5O_2]C_6H_4O]_2PN(C_2H_5)_2$, as a white solid (9.33 gm). $^{31}$P NMR (CDCl$_3$): 141.9 ppm.

The phosphoramidite (9.33 gm, 18.0 mmol) was dissolved in dry ether (150 mL) then cooled to −35° C. in a drybox freezer. Hydrogen chloride in dry ether (36 mL, 1.0 M) was added dropwise over a 20 minute period to the cold, stirred phosphoramidite solution. The resulting mixture was returned to the freezer for another 1.5 hours. The solids were vacuum filtered and washed with dry ether (20 mL). The combined ether filtrates were evaporated to yield the phosphorochioridite of acetal C, $[2-[5,5-(CH_3)_2-1,3-C_3H_5O_2]C_6H_4O]_2PCl$. $^{31}$P NMR (CDCl$_3$): 163.9 ppm.

Di(2,6-dimethylphenyl) 2,2'-dihydroxy-1,1'-binaphthalene-3,3'-dicarboxylate (0.792 gm, 1.36 mmol) was added to the phosphorochloridite of acetal C (1.634 gm, 3.40 mmol) dissolved in dry ether (50 mL). After cooling to −35° C. in a drybox freezer, the light yellow mixture was stirred as dry triethylamine (0.344 gm, 3.39 mmol) was added dropwise over a 5 minute period. After stirring at ambient temperature for another 2.5 hours, the mixture was filtered through dry, neutral alumina and the alumina was rinsed with dry tetrahydrofuran (50 mL). The combined filtrates were evaporated to yield the desired diphosphite ligand as a light yellow solid (0.376 gm). $^{31}$P NMR (CDCl$_3$): 129.7 ppm.

EXAMPLE 15

Synthesis of Ligand G

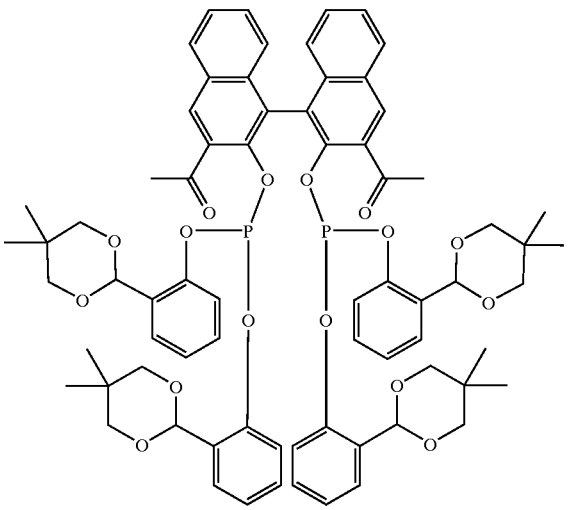

With stirring under dry nitrogen, 2,2'-dihydroxy-1,1'-binaphthalene-3,3'-dicarboxylic acid (1.87 gm, 5.0 mmol) was dissolved in dry tetrahydrofuran (50 mL) then cooled to −78° C. with a dry ice/acetone bath. Methyllithium (25 mL of 1.4 M in ether, 35 mmol) was added dropwise then the solution was allowed to warm to ambient temperature. After stirring overnight, the solution was added slowly to ice cold, 1 M hydrochloric acid (30 mL). The organic phase was washed with water then evaporated. The orange residue was dissolved in dichloromethane and eluted through a silica gel plug. The orange filtrate was evaporated to yield 2,2'-dihydroxy-1,1'-binaphthalene-3,3'-bis(methylketone) as a yellow solid (1.52 gm).

2,2'-Dihydroxy-1,1'-binaphthalene-3,3'-bis (methylketone) (0.200 gm, 0.54 mmol) was added to the phosphorochloridite of Acetal C (0.651 gm, 1.35 mmol) dissolved in dry ether (50 mL). After cooling to −35° C. in a drybox freezer, the light yellow mixture was stirred as dry triethylamine (0.155 gm, 1.53 mmol) was added dropwise over a 5 minute period. After stirring at ambient temperature for another 48 hours, the mixture was filtered through dry, neutral alumina and the alumina was rinsed with dry ether (50 mL). The combined filtrates were evaporated to yield the desired diphosphite ligand as a light yellow solid (0.466 gm). $^{31}$P NMR (CDCl$_3$): 134.1 ppm.

EXAMPLE 16

Synthesis of Ligand H

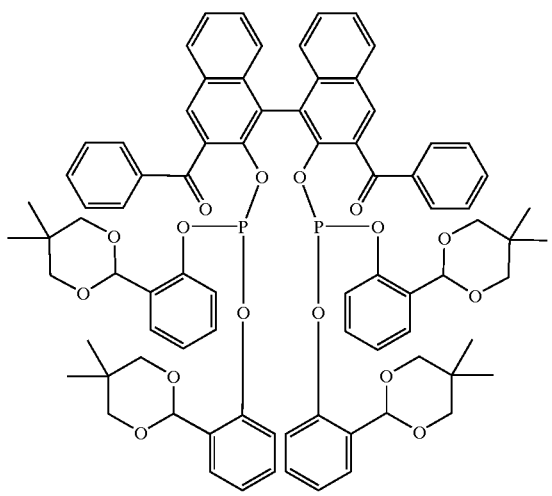

With stirring under dry nitrogen, 2,2'-dihydroxy-1,1'-binaphthalene-3,3'-dicarboxylic acid (8.42 gm, 22.5 mmol) was dissolved in dry tetrahydrofuran (500 mL) then cooled to −78° C. with a dry ice/acetone bath. Phenyllithium (100 mL of 1.8 M in 70/30 cyclohexane/ether, 0.18 mol) was added dropwise then the solution was allowed to warm to ambient temperature. After stirring overnight, deionized water (50 mL) was slowly added to the reaction solution at 0° C. With vigorous stirring, 1 M hydrochloric acid was added dropwise until the water phase became strongly acidic (pH=2). The organic phase was washed with water in a separatory funnel then dried over magnesium sulfate and evaporated. The orange residue was redissolved in dichloromethane and eluted through a silica gel plug. The orange filtrate was evaporated to yield 2,2'-dihydroxy-1,1'-binaphthalene-3,3'-bis(phenylketone) as a yellow solid (10.5 gm). 2,2'-Dihydroxy-1,1'-binaphthalene-3,3'-bis(phenylketone) (0.715 gm, 1.45 mmol) was added to the phosphorochloridite of Acetal C (1.738 gm, 3.62 mmol) dissolved in dry ether (50 mL). After cooling to −35° C. in a drybox freezer, the orange solution was stirred as dry triethylamine (0.365 gm, 3.62 mmol) was added dropwise over a 5 minute period. After stirring at ambient temperature for another 2.5 hours, the yellow mixture was filtered through dry, neutral alumina and the alumina was rinsed with dry ether (50 mL). The combined filtrates were evaporated to yield the desired diphosphite ligand as a light yellow solid (1.68 gm). $^{31}$P NMR (CDCl$_3$): 134.0 ppm.

EXAMPLE 17

Synthesis of Ligand I

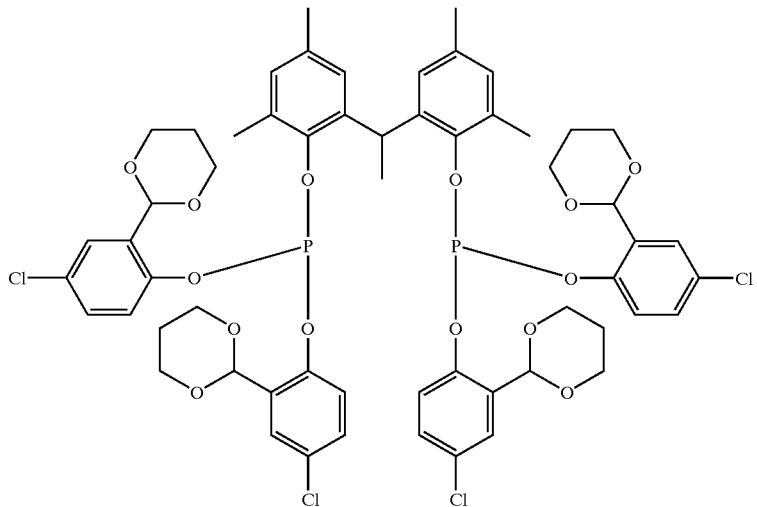

Into a round bottom flask was added 0.412 g of phosphorus trichloride and about 50 mL of toluene. The mixture was cooled to −30° C. and 1.288 g of Acetal G was added. A precooled solution (−30° C.) of triethylamine (0.800 g) in 20 mL of toluene was added dropwise. A $^{31}$P NMR of the mixture indicated a major resonance at 164.1 ppm with minor resonances at 193.3 and 132.5 ppm. To this mixture was added 0.405 g of 2,2'-ethylidenebis(4,6-dimethylphenol), prepared according to Yamada et al., *Bull. Chem. Soc. Jpn.*, 1989, 62, 3603, in 10 mL of toluene and then 0.600 g of triethylamine. The mixture was stirred overnight and then filtered through Celite®, washed with toluene, and solvent removed by rotary evaporation to yield the 1.8 g of a white solid $^{31}$P{H} (202 MHz, C$_6$D$_6$): major resonance at 134.9 ppm, minor resonances at 132.6, 132.2, 130.9, 128.2 ppm. APCI MS (atmospheric pressure chemical ionization mass spectroscopy): Found: 1183.1; calculated for C$_{58}$H$_{60}$O$_{14}$Cl$_4$P$_2$+H$^+$: 1183.22.

EXAMPLE 18

Synthesis of Ligand J

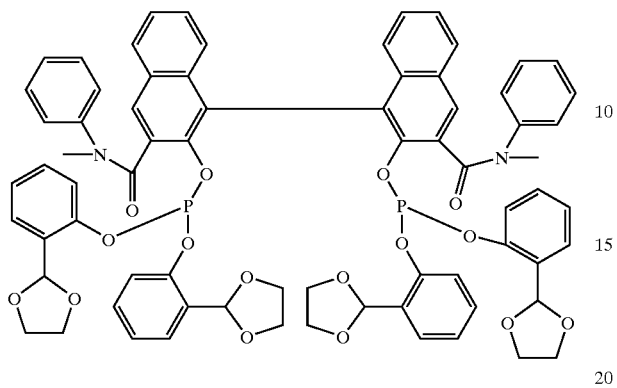

Acetal A (1.33 g, 8 mmol) and PCl$_3$ (0.55 g, 4 mmol) were dissolved in toluene (40 mL) and cooled to −40° C. A solution of Et$_3$N (1.0 g, 10 mmol) in toluene (15 mL) was added dropwise to the cold solution. The reaction was allowed to warm to room temperature then stirred overnight. A solution of (N-methyl, N-phenyl)-2,2'-dihydroxy-1,1'-binaphthalene-3,3'-dicarboxamide (1.1 g, 2 mmol) and Et$_3$N (0.4 g, 4 mmol) in toluene (15 mL) was added and the mixture was stirred for 2 hours. The mixture was filtered through Celite®, and the solvent was removed to give 2.3 g of a yellow sticky product. $^{31}$P NMR: δ 131.6, smaller peak at 127.6, broad peaks at 133.1, 144.1ppm.

EXAMPLE 19

Synthesis of Ligand K

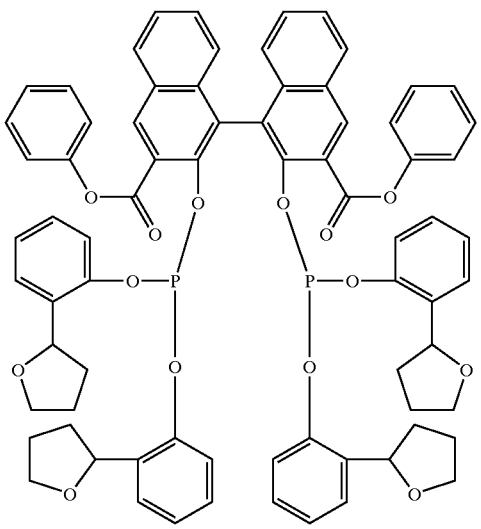

With stirring under a dry, nitrogen atmosphere, 2-(tetrahydro-2-furanyl)phenol (5.10 gm, 31.1 mmol) was added dropwise to N,N-diethylphosphoramidous dichloride (2.702 gm, 15.5 mmol) and dry triethylamine (3.77 gm, 37.3 mmol) dissolved in 200 mL of dry ether. After one hour, the triethylammonium chloride solids were vacuum filtered and washed with dry ether (3×15 mL). The combined ether filtrates were evaporated to yield the desired phosphoramidite, [2-(2-C$_4$H$_7$O)C$_6$H4O]$_2$PN(C$_2$H$_5$)$_2$, as a viscous oil. $^{31}$P NMR (CDCl$_3$): 142.2, 142.0, 141.5, and 141.2 ppm due to a mixture of stereoisomers.

The phosphoramidite (5.0 gm, 11.6 mmol) was dissolved in dry ether (50 mL) then cooled to −35° C. in a drybox freezer. Hydrogen chloride (24 mL, 1.0 M in dry ether) was added dropwise to the cold, stirred phosphoramidite solution. Five minutes after the addition was complete, the solids were vacuum filtered and washed with dry ether (3×15 mL). The combined ether filtrates were evaporated to yield the phosphorochloridite of 2-(tetrahydro-2-furanyl)phenol, [2-(2-C$_4$H$_7$O)C$_6$H$_4$O]$_2$PCl. $^{31}$P NMR (C$_6$D$_6$): 163.7, 162.9, 162.5ppm due to a mixture of stereoisomers.

Diphenyl 2,2'-dihydroxy-1,1'-binaphthalene-3,3'-dicarboxylate (0.425 gm, 0.807 mmol) was added to the phosphorochloridite of 2-(tetrahydro-2-furanyl)phenol (0.793 gm, 2.02 mmol) dissolved in dry ether (50 mL). After cooling to −35° C. in a drybox freezer, the light yellow mixture was stirred as dry triethylamine (0.204 gm, 2.02 mmol) was added dropwise over a 10 minute period. The mixture was filtered through dry, neutral alumina and the alumina was rinsed with dry ether (3×25 mL). The combined ether filtrates were evaporated to yield the desired diphosphite ligand as a white solid (0.81 gm). $^{31}$P NMR (C$_6$D$_6$): several peaks centered at 131 ppm due to a mixture of stereoisomers.

EXAMPLE 20

Synthesis of Ligand L

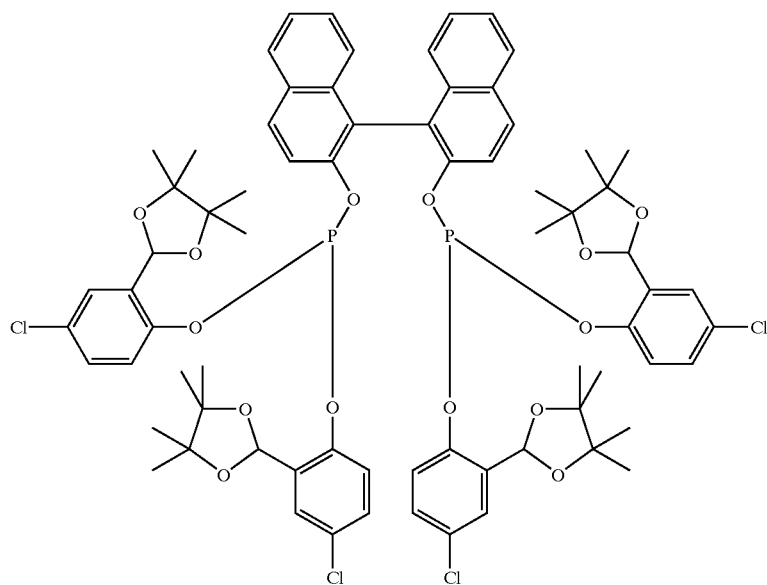

Into a round bottom flask was added 0.343 g of phosphorus trichloride and about 50 mL of toluene. The mixture was cooled to −30° C. and 1.284 g of acetal F was added. A precooled solution (−30° C.) of triethylamine (0.700 g) in 20 mL of toluene was added dropwise. A $^{31}$P NMR analysis of the mixture indicated a major resonance at 162.6 ppm with minor resonances at 190.4 and 130.7 ppm. To this mixture was added 0.358 g of 2,2'-binaphthol in 10 mL of toluene and then 0.600 g of triethylamine. The mixture was stirred overnight and then filtered through Celite®, washed with toluene and solvent removed by rotary evaporation to give 1.753 g of a white solid. $^{31}$P {H} (202 MHz, $C_6D_6$): major resonance at 130.0 ppm, other resonances at 143.1 and 130.8 ppm. APCI MS: Found: 1366.3; calculated for $C_{72}H_{76}O_{14}Cl_4P_2$: 1366.346.

EXAMPLE 21

Synthesis of Ligand M

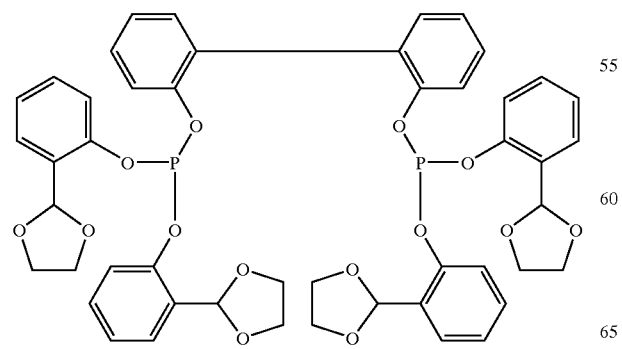

Acetal A (1.33 g, 8 mmol) and PCl$_3$ (0.55 g, 4 mmol) were dissolved in toluene (40 mL) and cooled to −40° C. A solution of Et$_3$N (1.0 g, 10 mmol) in toluene (15 mL) was added dropwise to the cold solution. The reaction was allowed to warm to room temperature then stirred overnight. A solution of 2,2'-biphenol (0.37 g, 2 mmol) and Et$_3$N (0.4 g, 4 mmol) in toluene (15 mL) was added and the mixture was stirred for 2 hours. The mixture was filtered through Celite®, and the solvent was removed to give 1.79 g of a pale, oily residue. $^{31}$P NMR: δ 131.3, smaller peaks at 132.5, 144.2 ppm,

EXAMPLE 22

Synthesis of Ligand N

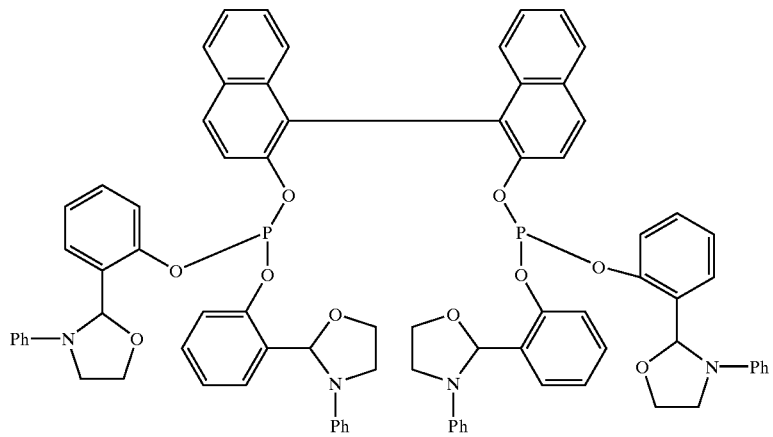

Amino-Acetal E (482 mg, 2.0 mmol) and Et$_3$N (0.67 g) were dissolved in toluene (10 mL). This solution was added to a −20° C. solution of PCl$_3$ (137 mg, 1 mmol) in toluene (3 mL) over a 5 minute period. After the addition, the mixture was stirred at −20° C. for 15 minutes. A suspension of 2,2'-binaphthol (143 mg, 0.5 mmol) and Et$_3$N (0.33 g) in toluene (5 mL) was added in one portion and the mixture was allowed to stir for 2 days. The mixture was filtered, and the solvent was evaporated to give 0.47 g of product. $^{31}$P NMR: δ 132.1, 130.8, small peaks at 147.2, 144.9 ppm.

EXAMPLE 23

Synthesis of Ligand O

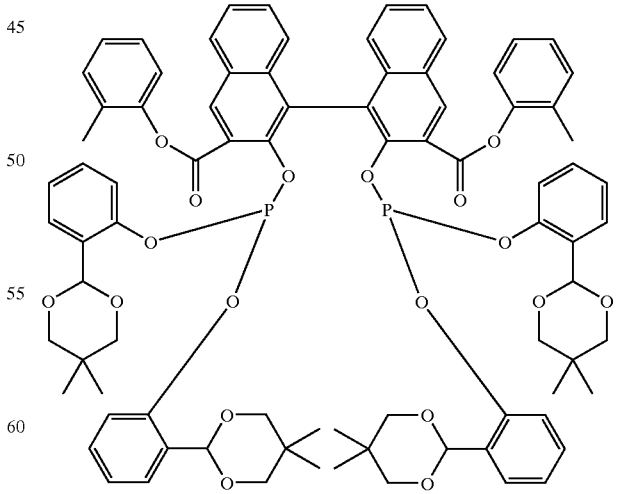

Acetal C (25.0 g, 120 mmol) and PCl$_3$ (8.23 g, 60 mmol) were dissolved in toluene (100 mL) and cooled to −20° C.

Approximately two-thirds of a Et$_3$N (21.0 g, 200 mmol) solution in toluene (100 mL) was added dropwise to the acetal solution over a 30 minute period. The mixture was stirred for another 15 min at −20° C. Over the next hour, small portions of solid di(2-tolyl)-2,2'-dihydroxy-1,1'-binaphthalene-3,3'-dicarboxylate (16.5 g, 29.8 mmol), were added to the cold, chloridite solution (−10 to −15° C.) while alternating with equivalent portions of the remaining Et$_3$N solution. The mixture was stirred for an hour, and the mixture was filtered. The solvent volume was reduced to between 100–200 mL toluene, and the solution was allowed to stand for 2 days. A fine white precipitate was collected (20.6 g). $^{31}$P NMR: δ 129.5 very small peaks at 133.1, 146.7 ppm.

EXAMPLE 24

Preparation of Carbon-supported Catalyst using Ligand O

Crystalline Rh(CO)$_2$(acac) (1 equiv), was dissolved into 2–4 mL toluene. The light-yellow solution was added to solid ligand O (100 mg), resulting in some bubbling and a change in solution color.

5 g of granular (40–60 mesh) activated carbon (EM Scientific) was dried and calcined by heating in flowing helium (100 mL/min) at 850° C. for 5 hrs. The dried carbon was transferred to a nitrogen filled glove box where it was slurried into a toluene solution containing rhodium and ligand O. The slurry was stirred for 15 min then evaporated to dryness in vacuum. Residual solids, deposited on the sides of the vessel, were rinsed with extra toluene such that all were eventually deposited only onto the carbon. The dry solid was pumped overnight to remove residual toluene and then capped and stored in the glove box for catalytic testing.

EXAMPLE 25

Synthesis of Ligand P

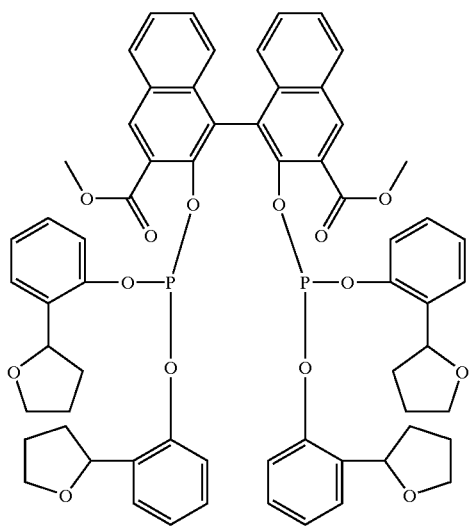

This diphosphite was prepared according to the general procedure described for ligand K except substituting the corresponding dimethyl ester for diphenyl 2,2'-dihydroxy-1,1'-binaphthalene-3,3'-dicarboxylate. The product was an oil. $^{31}$P NMR (C$_6$D$_6$): 131.0, 130.9, 130.8, 130.6, 130.4, 130.3 ppm due to a mixture of stereoisomers along with cyclic monophosphite impurity at 146.8 and 146.4 ppm.

EXAMPLE 26

Ligand O—Synthesis of Polymer Supported Ligand Preparation of a Supported Disubstituted Binaphthol

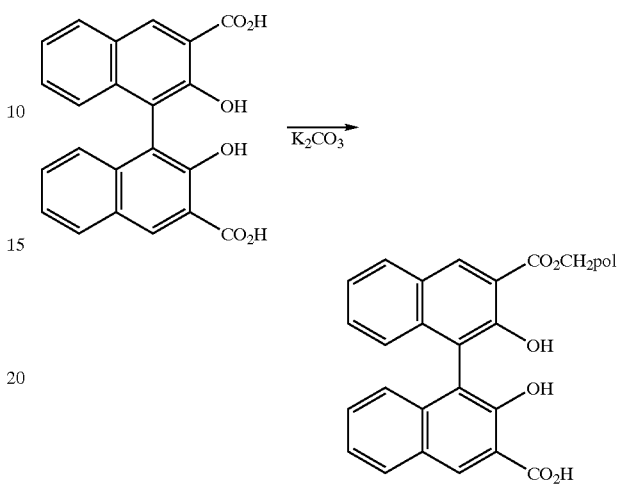

A mixture of 50 g (60 mmol) of Merrifield resin (polCH$_2$Cl where pol=1–2% crosslinked polystyrene, 200–400 mesh beads), 2,2'-dihydroxy-1,1'-binaphthalene-3,3'-dicarboxylic acid (33.7 g), potassium carbonate (12.4 g) and DMF (dimethylformamide) (350 ml) was heated at 90° C. with stirring for 8 hrs. The color of the resin changed from white to green-yellow. The mixture was diluted with water, filtered, washed with H$_2$0, DMF, and acetone, and then thoroughly dried in the air to give the desired product. IR (KBr, cm$^-$): 1712 (vs), 1676 (vs).

Functionalization of the Carboxylate Group

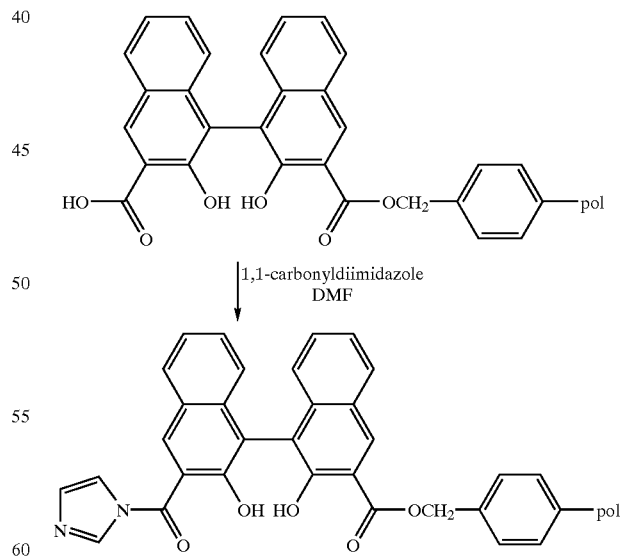

25 g (18.7 mmol) of the polymer supported diol was suspended in 150 mL of anhydrous DMF, and to this mixture was added 4.54 g (28 mmol) of 1,1-carbonyidiimidazole. The mixture was shaken overnight, and the polymer beads turned deep red-orange. The beads were collected by filtration and washed with DMF (3×100 mL), toluene (3×100 mL), and CH$_2$Cl$_2$ (3×100 mL) before drying under vacuum. IR (cm$^-$, KBr): 1771 (vs), 1720 (vs).

Esterification of the Side Chain

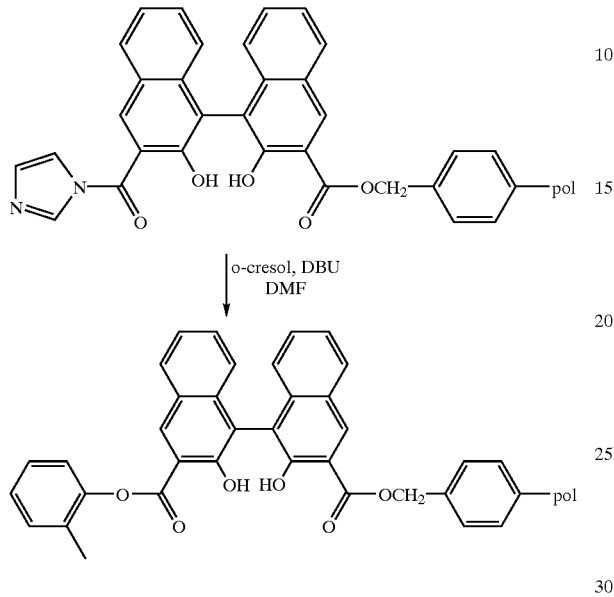

25.93 g (18.7 mmol) of the polymer supported imidazolyl ester was suspended in 150 mL of anhydrous DMF. 10.10 g (93.5 mmol) of ortho-cresol and 2.845 g (18.7 mmol) of DBU (1,8-Diazabicyclo[5.4.0]undec-7-ene) were added. The mixture was shaken for two days at room temperature. The product was collected by filtration and washed with DMF, toluene, and CH$_2$Cl$_2$ (3×100 mL) before final vacuum drying. IR (cm$^{-1}$, KBr): 1759 (w), 1720 (w), 1675 (vs).

Synthesis of Ligand Q

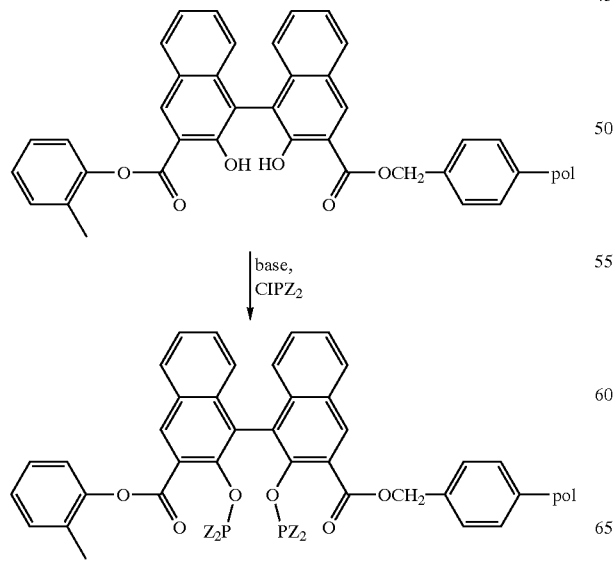

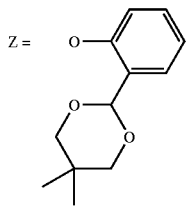

24.8 g (7.4 mmol) of the supported diol was suspended in 150 mL of toluene, and to this suspension was added 25.0 g (52.1 mmol) of the phosphorochloridite derived from acetal C and 13.4 g of diisopropylethylamine. The mixture was shaken overnight at room temperature. The pale yellow beads were collected by filtration, washed with toluene, CH$_2$Cl$_2$ (3×100 mL), and then dried under vacuum. Elemental analysis: 1.15 wt % P (average).

EXAMPLE 27

Synthesis of Ligand R

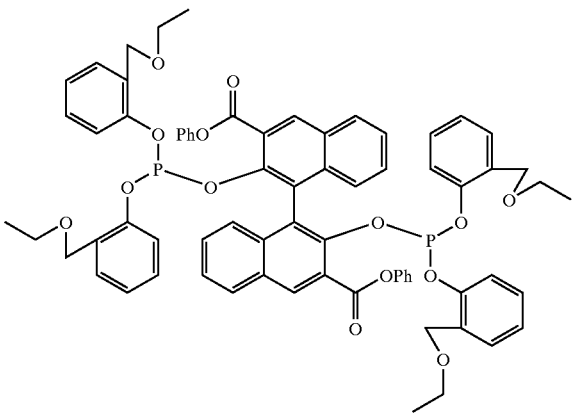

The ethyl ether of 2-hydroxybenzyl alcohol was prepared according to a literature procedure reported in *Recueil. Trav. Chim. Pays-Bas* 1955, 74, 1448. The phosphorochloridite of this phenol was prepared from PCl$_3$ in toluene with triethylamine as base at −30° C. $^{31}$P nmr of the reaction mixture: 163.3 ppm. To this mixture was added diphenyl 2,2′-dihydroxy-1,1′-binaphthalene-3,3′-dicarboxylate and triethylamine. The mixture was filtered through Celite® and the solvent removed by rotary evaporation. The residue was dissolved in toluene and passed through basic alumina with toluene. Solvent was removed and the residue vacuum dried. $^{31}$P {H} NMR (202.4 MHz, CDCl$_3$): major peak at 130.8 ppm other resonances at 146.9 and 132.4 ppm.

EXAMPLE 28

Synthesis of Ligand S

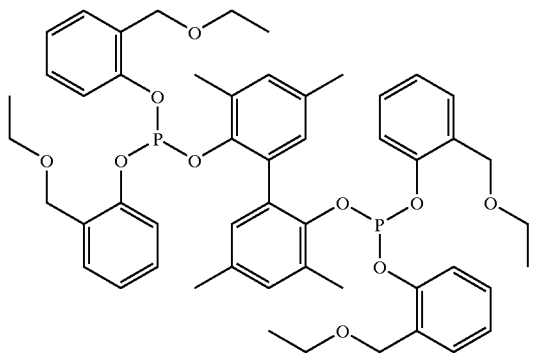

The procedure was the same as in example 27 (ligand R), except 3,3',5,5'-tetramethyl-2,2'-biphenol was used instead of diphenyl 2,2'-dihydroxyl-1,1'-binaphthalene-3,3'-dicarboxylate. $^{31}$P {H} NMR (202.4 MHz, CDCl$_3$): major peak at 133.5 ppm with minor resonances at 142.0 and 130.9 ppm.

EXAMPLE 29

Synthesis of Ligand T

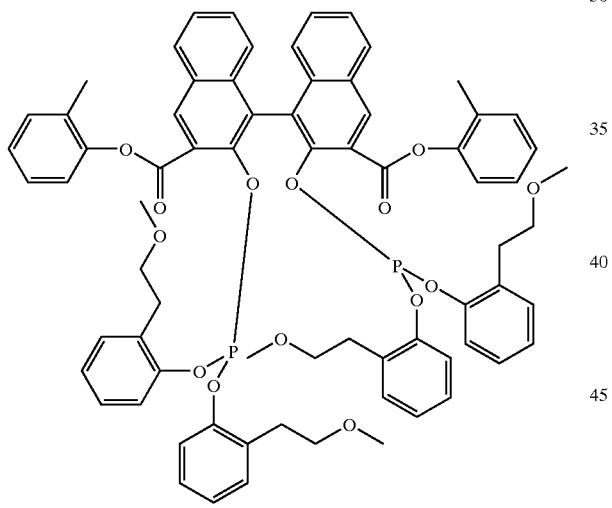

2-Hydroxyphenethyl alcohol was reacted with bromoacetonitrile in the presence of potassium carbonate to protect the phenolic oxygen, as in Tetrahedron Letters, 1993, 34, 7567–7568. 2-Hydroxyphenethyl alcohol was dissolved in 20 mL acetone. To this was added 1.2 g potassium carbonate. To the stirring mixture was added 0.87 g bromoacetonitrile under nitrogen. The mixture was stirred overnight. The mixture was filtered, and the filtrate was concentrated. The product was purified by flash column chromatography on silica gel, eluting with 1/1 ethyl acetate:hexanes, to yield 81% of 2-(o-cyanomethyl)phenethyl alcohol. $^1$H NMR (CD$_2$Cl$_2$): 2.81 (t, 2H), 3.72 (t, 2H), 4.77 (s, 2H), 6.92 (dd, 2H), 7.18 (d, 2H). 2-(o-Cyanomethyl)phenethyl alcohol (1.0 g, 6.3 mmol) was dissolved in 5 mL anhydrous DMF and added to a stirring solution of sodium hydride (0.25g, 10.4 mmol) in DMF (20 mL). After hydrogen evolution ceases, methyl iodide (0.47 mL, 7.5 mmol) was added dropwise. The mixture was stirred at room temperature under nitrogen for five hours. After aqueous workup, the product was purified using flash column chromatography on silica gel, eluting with 1/5 ethyl acetate/hexanes solvent mixture to yield 0.56 g (56%) of the desired product, 2-(o-cyanomethyl)phenethyl methyl ether. $^1$H NMR (CD$_2$Cl$_2$): 2.96 (t, 2H), 3.36 (s, 3H), 3.60 (t, 2H), 4.86 (s, 2H), 7.04 (dd, 2H), 7.31 (d, 2H).

2-(o-Cyanomethyl)phenethyl methyl ether was deprotected following the procedure described in Tetrahedron Letters, 1993, 34, 7567–7568. 2-(o-Cyanomethyl)phenethyl methyl (0.56 g, 3.13 mmol) was dissolved in 40 mL anhydrous ethanol. Platinum dioxide (20 mg) was added to this solution. The solution was purged with hydrogen for 10 minutes, and then stirred under hydrogen overnight. The mixture was filtered, and the filtrate was concentrated. The residue was redissolved in ether, washed with water, and dried over MgSO$_4$. After concentration, 0.39 g (82%) of 2-hydroxyphenethyl methyl ether was isolated. $^1$H NMR (CD$_2$Cl$_2$): 2.78 (t, 2H), 3.32 (s, 3H), 3.60 (t, 2H).

2-Hydroxyphenthyl methyl ether was reacted with diethylphosphoramidous dichloride to yield the corresponding phosphorous amidite in the same manner as described for Example 25. $^{31}$P NMR (toluene): 137 ppm. The phosphoroamidite was treated with 1M HCl solution following the procedure described for Example 25 to yield the corresponding phosphorochloridite. $^{31}$P NMR (toluene): 165 ppm. The phosphochloridite was then reacted with di(2-tolyl)-2,2'-dihydroxy-1,1'-binaphthalene-3,3'-dicarboxylate in the same manner as described for Example 19. $^{31}$P NMR (toluene): 125 (major), 127 (minor), 142 (minor).

EXAMPLE 30

Synthesis of Ligand U

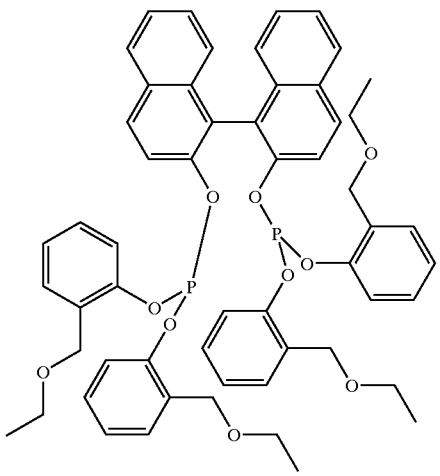

The ethyl ether of 2-hydroxybenzyl alcohol was prepared as described in Example 27. The phosphorochloridite of this phenol was prepared from PCl$_3$ in toluene with triethylamine as base at −30° C. $^{31}$P nmr of the reaction mixture: 158, 125 ppm. To the phosphorochloridite solution was added 2,2'-binapthol in the presence of triethylamine, as described in example 27. $^{31}$P NMR (toluene): 131 ppm (major), 146 (minor).

EXAMPLE 31

Synthesis of Ligand V

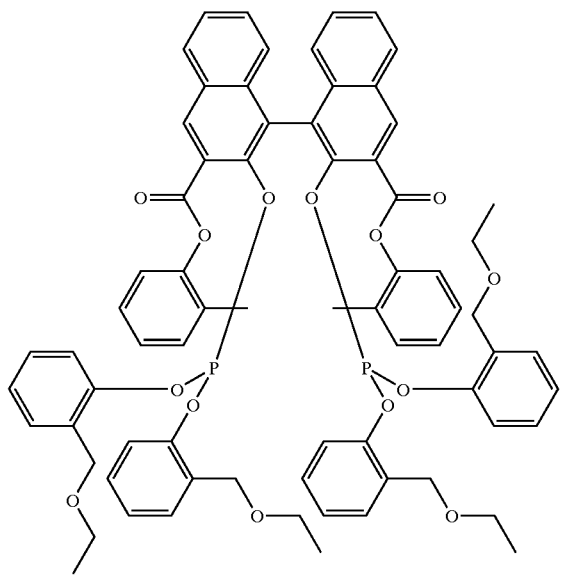

The ethyl ether of 2-hydroxybenzyl alcohol was prepared as described in Example 27. The phosphorochloridite of this phenol was prepared from PCl$_3$ in toluene with triethylamine as base at −30° C. $^{31}$P nmr of the reaction mixture: 158, 125 ppm. To the phosphorochloridite solution was added di(2-tolyl)-2,2'-dihydroxy-1,1'-binaphthalene-3,3'-dicarboxylate in the presence of triethylamine, as described in example 27. $^{31}$P NMR (toluene): 131 (major), 146 (minor), 163 (minor).

EXAMPLE 32

Synthesis of Ligand W

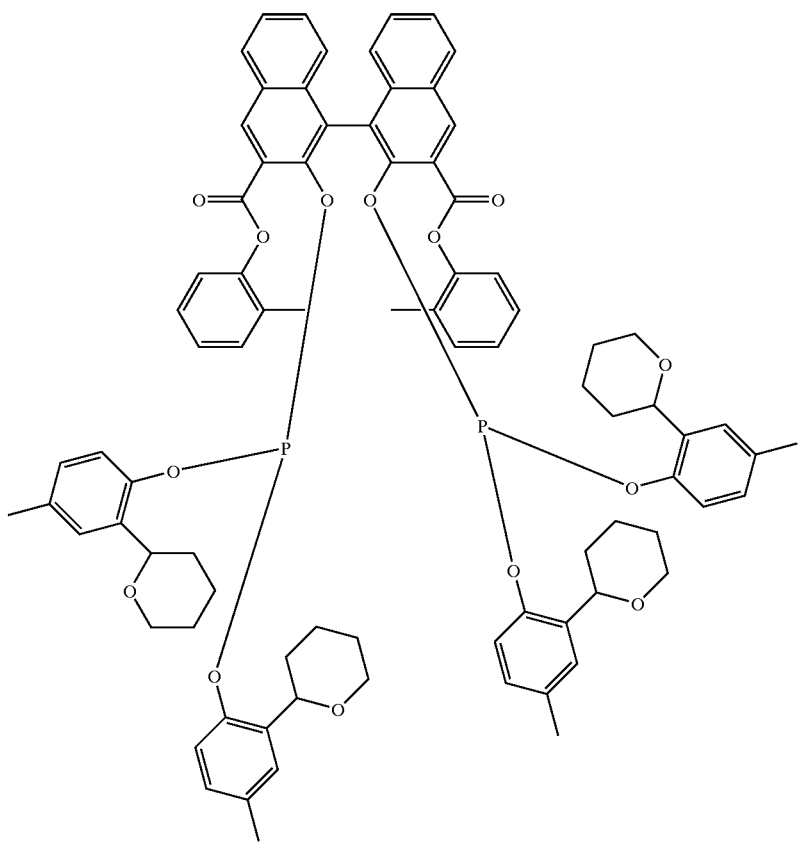

2-(2-Tetrahydropyranyl)-4-methyl-phenol was prepared from the corresponding phenol following the procedure outlined in *Aust. J. Chem.*, 1988, 41, 69–84. In a nitrogen purged glove box, 2-(2-tetrahydropyranyl)-4-methyl-phenol (0.96 g, 5.0 mmol) was dissolved in 25 ml diethyl ether, and cooled to −40° C. Diethylphosphoramidous dichloride (2.5 mmol) was added, followed by triethylamine (6 mmol). The reaction mixture was stirred at room temperature for one hour, then filtered over a pad of Celite®. The filtrate was concentrated in vacuo to yield 1.1 g (90%) of the corresponding phosphorous amidite. $^{31}$P NMR (toluene): 142.7, 142.6. The above phosphorous amidite (1.1 g) was dissolved in 25 mL anhydrous ether and cooled to −40° C. To the stirring phosphoramidite solution was slowly added 4.4 mL of precooled 1M HCl solution in ether. Upon addition, white precipitate formed. The mixture was stirred for 10 minutes, and cooled back to 40° C. for 2 hours. The resulting slurry was filtered over a pad of Celite®, and concentrated in vacuo to yield 0.92 g of the corresponding phosphorochloridite. $^{31}$P NMR (toluene): 161.6 ppm. The above phosphorochloridite was reacted with di(2-tolyl)-2,2'-dihydroxy-1,1'-binaphthalene-3,3'-dicarboxylate and triethylamine to yield the corresponding ligand. $^{31}$P NMR (toluene): 130 (major).

EXAMPLE 33

Synthesis of Ligand X

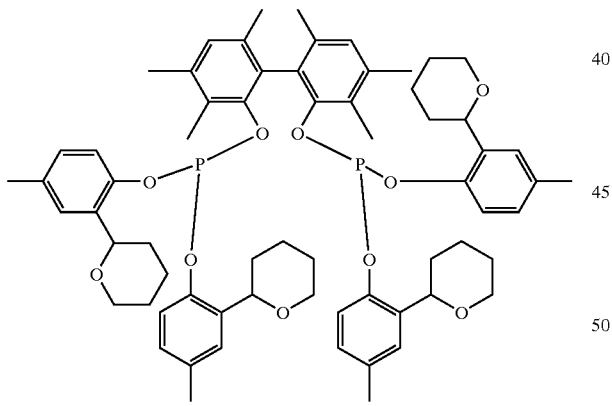

The phosphorochloridite of 2-(2-tetrahydropyranyl)-4-methyl-phenol was prepared as described in example 32. The above phosphorochloridite was reacted with 3,3',4,4',6,6'-hexamethyl-2,2'-biphenol and triethylamine to yield the corresponding ligand. $^{31}$P NMR (toluene): 134, 131, 127.

EXAMPLE 34

Synthesis of Ligand Y

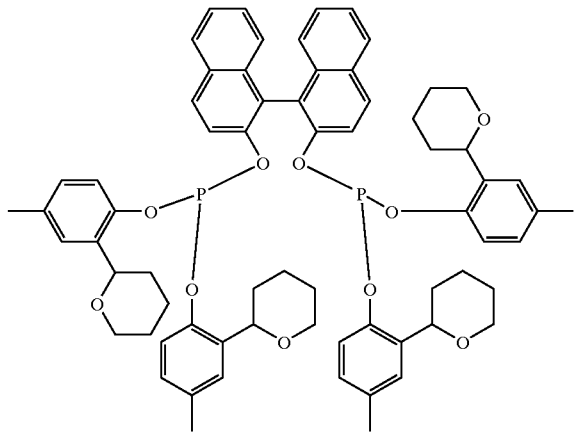

2-(2-Tetrahydropyranyl)-4-methyl-phenol was prepared from the corresponding phenol following the procedure outlined in *Aust. J. Chem*, 1988, 41, 69–84. In a nitrogen purged glove box, 2-(2-tetrahydropyranyl)-4-methyl-phenol (0.96 g, 5.0 mmol) was dissolved in 25 ml diethyl ether, and cooled to −40° C. Diethylphosphoramidous dichloride (2.5 mmol) was added, followed by triethylamine (6 mmol). The reaction mixture was stirred at room temperature for one hour, then filtered over a pad of Celite®. The filtrate was concentrated in vacuo to yield 1.1 g (90%) of the corresponding phosphorous amidite. $^{31}$P NMR (toluene): 142.7, 142.6. The above phosphorous amidite (1.1 g) was dissolved in 25 mL anhydrous ether and cooled to 40° C. To the stirring phosphorous amidite solution was slowly added 4.4 mL of precooled 1M HCl solution in ether. Upon addition, a white precipitate formed. The mixture was stirred for 10 minutes, and cooled to −40° C. for 2 hours. The resulting slurry was filtered over a pad of Celite®, and concentrated in vacuo to yield 0.92 g of the corresponding phosphorochloridite. $^{31}$P NMR (toluene): 161.6 ppm. The above phosphorochloridite was reacted with 1,1'-bi-2-napthol and triethylamine to yield the corresponding ligand. $^{31}$P NMR (toluene): 131.11, 131.14 (stereoisomers).

COMPARATIVE EXAMPLE A

Synthesis of Ligand Z

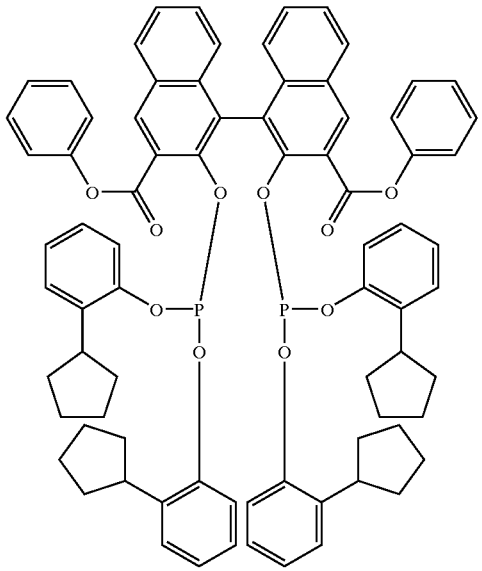

With stirring under a dry, nitrogen atmosphere, 2-cyclopentylphenol (4.10 gm, 25.3 mmol) was dissolved in dry ether (15 mL) then added dropwise to N,N-diethylphosphoramidous dichloride (2.00 gm, 11.5 mmol) and dry triethylamine (3.26 gm, 32.2 mmol) dissolved in 50 mL of dry ether. After stirring two hours, the triethylammonium chloride solids were vacuum filtered and washed with dry ether (2×15 mL). The combined ether filtrates were evaporated to yield the desired phosphoramidite, [2-($C_5H_9$)$C_6H_4O$]$_2$PN($C_2H_5$)$_2$, as an oil.

The phosphoramidite (2.13 gm, 5.0 mmol) was dissolved in dry ether (50 mL) then cooled to −35° C. in a drybox freezer. Hydrogen chloride in dry ether (10.0 mL, 1.0 M) was added dropwise over a 5 minute period to the cold, stirred phosphoramidite solution to generate the phosphorochloridite of 2-cyclopentylphenol, [2-($C_5H_9$)$C_6H_4O$]$_2$PCl. The resulting solids were vacuum filtered and washed with dry toluene (2×5 mL). The combined ether/toluene filtrates were concentrated to 50 mL volume.

Dry triethylamine (1.01 gm, 10 mmol) was added to the ether/toluene solution followed by diphenyl 2,2'-dihydroxy-1,1'-binaphthalene-3,3'-dicarboxylate (1.05 gm, 2.0 mmol). After stirring overnight in the drybox, the solids were vacuum filtered then washed with dry toluene (3×5 mL). The combined filtrates were evaporated to yield the diphosphite. $^{31}$P NMR (CDCl$_3$): 132.0 ppm. LC/MS (APCI+): m/e=1231.

COMPARATIVE EXAMPLE B

Synthesis of Ligand AA

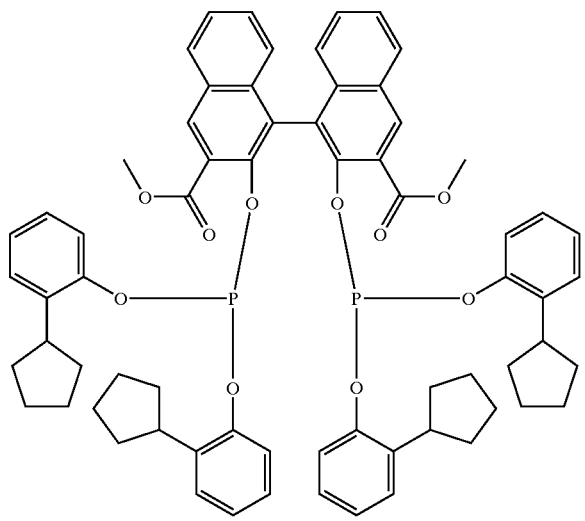

This diphosphite was prepared according to the general procedure described for ligand Z except substituting the corresponding dimethyl ester for diphenyl 2,2'-dihydroxy-1,1'-binaphthalene-3,3'-dicarboxylate. $^{31}$P NMR (CDCl$_3$): 131.5 ppm along with a monodentate phosphite impurity at 129.2 ppm.

EXAMPLE 35

Hydroformylation of 3-Pentenenitrile (3PN) using Ligand A

In the drybox was prepared a solution containing 3-pentenenitrile (3PN) (0.5 M), rhodium bis(carbonyl) acetylacetonate (Rh(acac)(CO)$_2$) (0.9 mM), and 1,2-dichlorobenzene (internal standard, 0.14 M) in toluene. A portion of this solution was added to a glass-lined pressure vessel containing approximately 49 equivalents of Ligand A/rhodium. The reactor was sealed, pressurized to 50 psi 1:1 CO/H$_2$ and heated to 95° C. for 3 hours. The reactor was cooled and depressurized and a sample of the reaction mixture was analyzed by gas chromatography on an HP 5890A Chromatograph with a Quadrics 23 fused silica capillary column (30 meters, 0.32 mm I.D., 0.25 um film thickness) purchased from the Quadrex Corporation. GC analysis: conversion of pentenenitriles: 69%; selectivity to 5-formylvaleronitrile: 77% on a mole basis; linearity of aldehydes produced: 94%.

EXAMPLE 36

Hydroformylation of 3PN using Ligand B

In the drybox was prepared a solution containing 3-pentenenitrile (0.5 M), Rh(acac)(CO)$_2$ (0.9 mM), and 1,2-dichlorobenzene (internal standard, 0.14 M) in toluene. A portion of this solution was added to a glass-lined pressure vessel and enough of a solution of the ligand (0.05 M) in toluene was added to give 2.7 equivalents of Ligand B/Rh. The reactor was sealed, pressurized to 55 psi 1:1 CO/H$_2$ and heated to 95° C. for 3 hours. The reactor was cooled and depressurized and a sample of the reaction mixture was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis: conversion of pentenenitriles: 94.7%; selectivity to 5-formylvaleronitrile: 60% on a mole basis; linearity of aldehydes produced: 73%.

EXAMPLE 37

Hydroformylation of 3PN using Ligand C

In the drybox was prepared 25 mL of a solution containing Rh(acac)(CO)$_2$ (2.4 mM) and Ligand C (6.8 mM), and triphenylphosphine oxide (internal standard, 2.1 mM) in toluene. This solution was loaded into a 100 mL Parr autoclave under a stream of H$_2$/CO. The autoclave was charged to 65 psi with 1:1 H$_2$/CO and heated to 95° C. Once the temperature had stabilized, 10.0 mL of a solution of 3-pentenenitrile (3.5 M) and o-dichlorobenzene (1.0 M, internal standard) in toluene was added via a high pressure syringe pump (Isco Series 260 D) over 1 minute. Then a continuous flow of 1:1 H$_2$/CO (approximately 30 cc/min) was provided to the reactor, maintaining a pressure of 65 psi. The mixture was stirred at approximately 900 rpm with an air-driven rotary stirrer for 80 minutes. Samples were withdrawn via a needle valve and analyzed by gas chromatography on an HP 5890A Chromatograph with a Quadrex 23 fused silica capillary column (30 meters, 0.32 mm I.D., 0.25 um film thickness) purchased from the Quadrex Corporation. After 80 minutes, GC analysis indicated conversion of pentenenitriles: 100%; selectivity to 5-formylvaleronitrile: 78% on a mole basis; linearity of aldehydes produced: 92%.

EXAMPLE 38

Hydroformylation of 3PN using Ligand J 0.203 g Rh(CO)$_2$(acac), 32.4 g 3PN and, 4.0 g 1,2-dichlorobenzene were mixed, and then toluene was added to make a stock solution of 400 mL total volume. 64 mg of Ligand J and 5 mL of the stock solution (ratio of P/Rh: 5: 1) were mixed and put into a glass vial. This mixture was heated to 95° C. under 75 psi (1:1 $H_2$:CO) for 3 hours. A sample was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis indicated conversion of pentenenitriles: 100%; selectivity to 5-formylvaleronitrile: 75% on a mole basis; linearity of aldehydes produced: 95%.

EXAMPLE 39

Hydroformylation of M3P using Ligand J

In the drybox was prepared a solution containing methyl-3-pentenoate (M3P) (0.5 M), Rh(acac)(CO)$_2$ (0.9 mM), and 1,2-dichlorobenzene (internal standard, 0.14 M) in toluene. A portion of this solution was added to a glass-lined pressure vessel and enough of a solution of the ligand (0.05 M) in toluene was added to give 4.6 equivalents of Ligand J/Rh. The reactor was sealed, pressurized to 55 psi 1:1 CO/H$_2$ and heated to 95° C. for 3 hours. The reactor was cooled and depressurized and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. Conversion of methyl-3-pentenoate: 84%; selectivity to methyl-5-formylvalerate: 78% on a mole basis; linearity of aldehydes produced: 98.8%.

EXAMPLE 40

Hydroformylation of 3PN using Ligand M 20.25 g 3PN, 0.125 g Rh(CO)$_2$(acac), and 2.5 g 1,2-dichlorobenzene were mixed to make a stock solution. Take 0.4575g (0.503 mL) of this stock solution to 10 mg of ligand M. No toluene added. Run same condition as above. (P:Rh: 2.5). A sample was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis indicated conversion of pentenenitriles: 85%; selectivity to 5-formylvaleronitrile: 55%; linearity of aldehydes produced:65%.

EXAMPLE 41

Hydroformylation of Methyl-3-Pentenoate(M3P) using Ligand M

In the drybox was prepared a solution containing methyl-3-pentenoate (0.5 M), Rh(acac)(CO)$_2$ (0.9 mM), and 1,2-dichlorobenzene (internal standard, 0.14 M) in toluene. A portion of this solution was added to a glass-lined pressure vessel and enough of a solution of the ligand (0.05 M) in toluene was added to give 2.5 equivalents of Ligand M/Rh. The reactor was sealed, pressurized to 55 psi 1:1 CO/H$_2$ and heated to 95° C. for 3 hours. The reactor was cooled and depressurized and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. Conversion of methyl-3-pentenoate: 74%; selectivity to methyl-5-formylvalerate: 57% on a mole basis; linearity of aldehydes produced: 70%.

EXAMPLES 42–53

Hydrofornylation of 3PN using Ligands D through I, and K, L, N, P, X, and Y

Example 36 was repeated with Ligands D through I, and K, L, N, P, X, and Y. The results are given in Table 1 below.

TABLE 1

Hydroformylation of 3-pentenenitrile by the above method

| Example | Ligand | Conv | Sel | Lin | L/M |
|---|---|---|---|---|---|
| 42 | D | 98 | 70 | 86 | 5.0 |
| 43 | E | 96 | 41 | 48 | 1.6 |
| 44 | F | 89 | 83 | 98 | 5.5 |
| 45 | G | 89 | 83 | 98 | 5.5 |
| 46 | H | 93 | 80 | 98 | 5.5 |
| 47 | I | 83 | 45 | 58 | 5.4 |
| 48 | K | 91 | 74 | 96 | 5.6 |
| 49 | L | 85 | 61 | 81 | 5.0 |
| 50 | N | 66 | 39 | 48 | 5.5 |
| 51 | P | 90 | 61 | 75 | 2.8 |
| 52 | X | 66 | 71 | 82 | 6.0 |
| 53 | Y | 80 | 53 | 64 | 6.0 |

EXAMPLE 54

Gas-Phase Hydroformylation of Propylene using Ligand O

An empty 0.25-inch (0.64 cm) diameter, 15-inch (37.5 cm) long stainless steel tubular reactor was placed in a nitrogen-filled drybox. A plug of glass wool was placed in the bottom end of the reactor, followed by 3 g of catalyst. A thermocouple was inserted into the top of the reactor. Both ends of the reactor were sealed by valves, and the reactor was removed from the drybox and was connected to stainless steel reactor feed lines purged with nitrogen. The reactor was equipped with a by-pass line to allow for a flow of CO and H$_2$ to be established before opening the inlet side of the reactor to the feed gases. The desired temperature of 100° C. was established in the reactor by means of a split tube furnace surrounding the reactor. When the desired temperature and flow rates of 2cc/min CO and 2cc/min H$_2$ feed gases had been achieved, a valve was turned to begin passing CO and H$_2$ over the catalyst. Periodically, at times shown in Table 2, reactor effluent samples were analyzed by gas chromatography for the amounts of unreacted propylene, linear and branched butyraldehyde.

Table 2 shows the g of catalyst and the wt% of phosphorus in the catalyst used. The mole ratio of Rh/P shown in Table 2 is the ratio used to complex Rh to the catalyst from a solution of Rh(acac)(CO)$_2$ in toluene. The TON/hr numbers shown in Table 2 were calculated to represent the moles of propylene reacted per mole of Rh per hour.

TABLE 2

Gas Phase Propylene/CO/H$_2$ Reactions

| ligand | Catalyst g, % P, Rh/P | Propene/ CO/H$_2$ cc/min. | Elapsed Time, hr | Propylene % Conv. | Linear/ Branched | TON/ hr |
|---|---|---|---|---|---|---|
| O | 3.0, 0.08,0.5 | 2,2,2 | 3.1 | 78.0 | | 106 |
| | | | 9.5 | 80.6 | >29 | 131 |
| | | | 32.8 | 78.4 | 68.5 | 104 |
| | | | 38.8 | 81.9 | 68.3 | 131 |
| | | | 50.3 | 81.7 | 68.5 | 103 |
| | | | 53.3 | 78.8 | 67.0 | 131 |

EXAMPLE 55

Hydroformylation of 3PN using a Polymer Supported Catalyst—Ligand O

A 100 mL autoclave equipped with a sampling line connected to a sintered frit was charged with 1.32 g of Ligand Q. The autoclave was evacuated and a solution containing 0.048 g of Rh(acac)(CO)$_2$ in 50 g of 3-pentenenitrile was loaded under vacuum. The mixture was stirred for 5 minutes and the liquid was removed from the autoclave via the sampling line by applying pressure. The solid remaining in the autoclave was rinsed with 3 portions of 50 ml of 3-pentenenitrile each following the same procedure. A solution containing 70 g of 3-pentenenitrile and 2 g of ortho-dichlorobenzene was loaded into the autoclave.

The autoclave was pressurized with 65 psi CO/H$_2$ (1:1), heated at 95° C. under vigorous stirring for 4 hours while flowing CO/H$_2$ at a rate of 20 mL/min for 4 hours. A sample was removed from the reactor after 4 hours and analyzed by GC (mole %): 2PN 2.4%, VN 18.8%, 3PN 5.6%, 5FVN 68.1%. 3PN conversion 94%, 5FVN selectivity 74%, aldehyde linearity 94.4%.

EXAMPLE 56

Hydroformylation of 3-Pentenenitrile using Ligand R

A solution containing 0.2536 g of Ligand R, 0.018 g of Rh(acac)(CO)$_2$, 1 g of 1,2-dichlorobenzene and 30 g of 3-pentenenitrile was loaded into a 100 mL autoclave and heated with vigorous stirring under 65 psi CO/H$_2$ (1:1) while flowing CO/H$_2$ at a rate of approximately 30 mL/min at 95° C. for 4.5 hours. The reactor was cooled and depressurized, and a sample of the reaction mixture was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis: 2-pentenenitrile 1.3%, valeronitrile 10.0%, 3-pentenenitrile 5.1%, 5-formylvaleronitrile 66.8%. Conversion of pentenenitriles: 95%; selectivity to 5-formylvaleronitrile: 71% on a mole basis; linearity of aldehydes produced: 80%.

EXAMPLE 57

Hydroformylation of 3-Pentenenitrile using Ligand S

The reaction was run as in example 56, but with 3.1 equivalents of Ligand S/Rh, for 5 hours. GC analysis: 2-pentenenitrile 0.1%, valeronitrile 17.9%, 3-pentenenitrile 0.1%, 5-formylvaleronitrile 58.7%. Conversion of pentenenitriles: 100%; selectivity to 5-formylvaleronitrile: 59% on a mole basis; linearity of aldehydes produced: 72%.

EXAMPLE 58

Hydroformylation of 1-Octene using Ligand S

In the drybox was prepared a solution containing 1-octene (0.89 M), Rh(acac)(CO)$_2$ (5.9 mM), and Ligand S (25 mM) in toluene. 1 mL of this solution was heated at 80° C. under 100 psi of CO/H$_2$ (1/1) for 1 hr. Butyl ether (2.5 mg, 0.02 mmole) was added into the mixture as the internal standard and the mixture was analyzed by gas chromatography (GC) with a Chrompack CP-SIL 8 column (30 m×0.32 mm ID). (mole %) 7.3% octane, 14.3% internal octenes, 14.4% 2-methyl octanal, 4.0% other branched aldehydes, and 52.3% nonanal. Conversion of 1-octene: 100%; selectivity to nonanal: 57%; linearity of aldehydes produced: 740).

EXAMPLE 59

Hydroformylation of 3-Pentenenitrile using Ligand T

The reaction was run as in example 56, but with 5.9 equivalents of Ligand T/Rh. GC analysis: (mole %) 2-pentenenitrile 18.5%, valeronitrile 6.5%, 3-pentenenitrile 42.0%, 5-formylvaleronitrile 23.6%. Conversion of pentenenitriles: 54%; selectivity to 5-formylvaleronitrile: 44% on a mole basis; linearity of aldehydes produced: 83%.

EXAMPLE 60

Hydroformylation of 1-Octene using Ligand U

The reaction was run as in example 58, but with Ligand U. GC analysis: (mole %) 3.8% octane, 31.0% internal octenes, 5.9% 2-methyl octanal, and 46.1% nonanal. Conversion of 1-octene: 100%; selectivity to nonanal: 53%; linearity of aldehydes produced: 89%).

EXAMPLE 61

Hydroformylation of 1-Octene using Ligand V

The reaction was run as in example 58, but with Ligand V. GC analysis: (mole %) 6.5% octane, 28.3% internal octenes, 7.0% 2-methyl octanal, and 50.4% nonanal. Conversion of 1-octene: 100%; selectivity to nonanal: 55%; linearity of aldehydes produced: 88%).

EXAMPLE 62

Hydroformylation of Methyl-3-Pentenoate using Ligand W

A solution containing 0.2600 g ligand W, 0.018 g of Rh(acac)(CO)$_2$, 1 g of ortho-dichlorobenzene and 30 g of methyl 3-pentenoate was loaded into a 100 mL autoclave and heated with vigorous stirring under 55 psi CO/H$_2$ (1:1) while flowing CO/H$_2$ at a rate of approximately 30 mL/min at 95° C. for 6.5 hours. The reactor was cooled and depressurized, and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. Conversion of methyl-3-pentenoate: 100%; selectivity to methyl 5-formylvalerate: 92% on a mole basis; linearity of aldehydes produced: 98%.

COMPARATIVE EXAMPLE A-I

Hydroformylation of 3-Pentenenitrile using Ligand Z

The procedure of Example 36 was followed for ligand Z. The data in Table 3 indicate that ligands C and P give higher selectivity to the desired product than ligand Z.

TABLE 3

| Ligand | Hydroformylation of 3-pentenenitrile | | | |
|---|---|---|---|---|
| | Conv | Sel | Lin | L/M |
| C | 100 | 80 | 93 | 5.0 |
| P | 91 | 74 | 96 | 5.6 |
| Z | 70 | 45 | 58 | 5.0 |

COMPARATIVE EXAMPLE B-I

Hydroformylation of 3-Pentenenitrile using Ligand AA

The procedure of Example 36 was followed for ligand AA. The data in Table 4 indicate that ligands A and K give higher selectivity to the desired product than ligand AA.

TABLE 4

| Ligand | Hydroformylation of 3-pentenenitrile | | | |
|---|---|---|---|---|
| | Conv | Sel | Lin | L/M |
| A | 69 | 77 | 94 | 10 |
| K | 90 | 61 | 75 | 2.8 |
| AA | 80 | 52 | 64 | 2.7 |

What is claimed is:

1. A hydroformylation process comprising reacting an unsaturated compound with CO and $H_2$ in the presence of a composition comprising a transition metal, and at least one multidentate phosphite ligand of the formulae I, I-A or I-B:

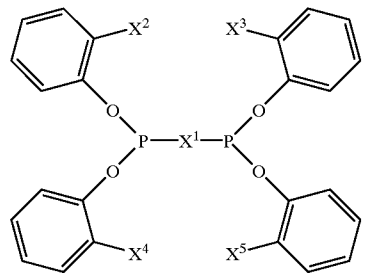

Formula I

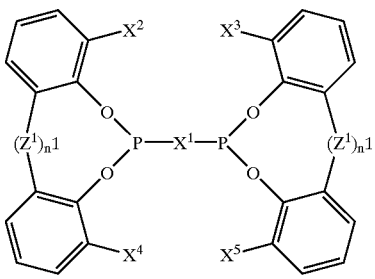

Formula I-A

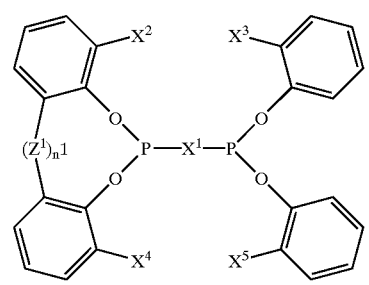

Formula I-B wherein $X^1$ is a bridging group selected from the group consisting of

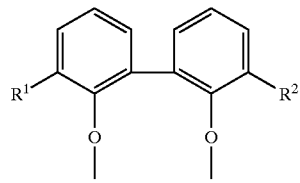

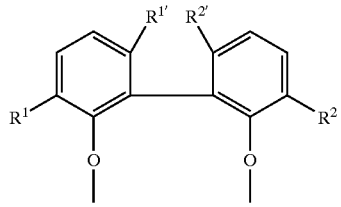

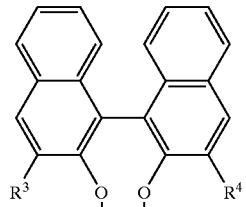

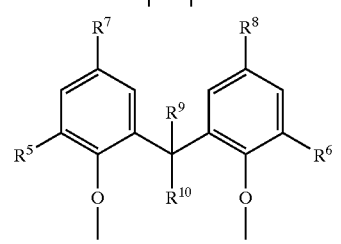

wherein $R^1$, $R^2$, $R^3$, $R^4$, $R^5$, $R^6$, $R^7$, $R^8$, $R^{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR_2^{12}$, acetal, ketal, dialkylamino, or diarylamino, —$OR^{11}$, —$CO_2R^{11}$, —$(CNR^{11})R^{11}$, —$(CNOR^{11})R^{11}$; wherein $R^{11}$ is $C_1$ to $C_{18}$ alkyl, cycloalkyl, aryl, or substituted aryl, —$C(O)R^{12}$, —$C(O)NR^{12}R^{13}$, —O—$C(O)R^{12}$, —$NR^{12}$—$C(O)R^{13}$; wherein $R^{12}$ and $R^{13}$ are independently selected from the group consisting of H, $C_1$ to $C_{18}$ alkyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR^{11}$, —$CO_2R^{11}$, $RCNR^{11}$, or $RCNOR^{11}$; and wherein $R^9$ and $R^{10}$ are independently selected from the group consisting of H, $C_1$ to $C_{18}$ alkyl, cycloalkyl, aryl, or substituted aryl;

wherein $X^2$ through $X^5$ are independently selected from the group consisting of:

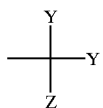

wherein Y is independently selected from the group consisting of H, aryl, $CR^{14}_3$, $(CR^{14}_2)n$—$OR^{14}$, $(CR^{14}_2)n$—$NHR^{15}$; wherein $R^{14}$ is H, $C_1$–$C_{18}$ alkyl, cycloalkyl, or aryl; wherein $R^{15}$ is selected from the group consisting of H, alkyl, cycloalkyl, aryl, —$SO_2R^{11}$, —$SO_2NR^{12}_2$, —$COR^{16}$; and wherein $R^{16}$ is H, $C_1$–$C_{18}$ alkyl, aryl, or perfluoroalkyl; wherein Z is selected from the group consisting of $(CR^{14}_2)_n$—$OR^{14}$; wherein n=0–3; and wherein, optionally, either one of the Y's may be linked with Z to form a cyclic ether;

wherein a ligand of the structure of Formula I-A or Formula I-B has at least one aromatic ring carbon in the ortho position to an O bonded to a P bonded through $(Z^1)n^1$ to another aromatic ring carbon in the ortho position to the other O bonded to the P; and wherein $Z^1$ is independently;

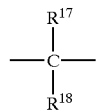

and wherein each $R^{17}$ and $R^{18}$ are independently selected from the group consisting of H, $C_1$ to $C_{18}$ alkyl, cycloalkyl, aryl, or substituted aryl; and $n^1$ is either one or zero.

2. The process of claim 1 wherein the ligand has either Y linked to Z to form a cyclic ether.

3. The process of claim 1 wherein the ligand has the structure of formula I.

4. The process of claim 1 wherein a Y is linked with Z to give the ligand at least one terminal group of the structure of formulae A or B; $Y^3$=O or $CH_2$; and $R^{14}$ is defined as above:

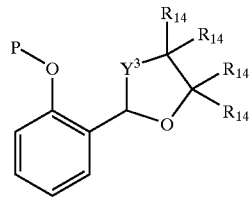

Formula A

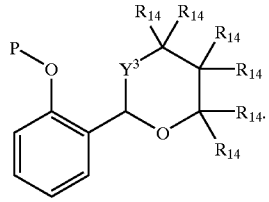

Formula B

5. The process of claim 1 wherein the reactants are in the liquid phase.

6. The process of claim 1 wherein the reactants are in the vapor phase.

7. The process of claim 1 wherein the unsaturated compound is an acyclic, monoethylenically unsaturated compound.

8. The process of claim 1 wherein the unsaturated compound is an acyclic, aromatic olefin compound.

9. The process of claim 7 wherein the acyclic, monoethylenically unsaturated compound has from 2 to 30 carbon atoms.

10. A hydroformylation process comprising reacting an unsaturated compound with CO and $H_2$ in the presence of a composition comprising a transition metal, and at least one multidentate phosphite ligand of the formulae II, II-A or II-B:

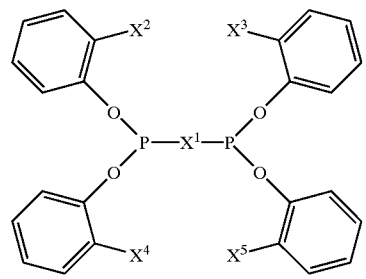

Formula II

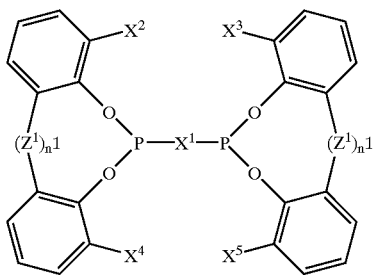

Formula II-A

-continued

Formula II-B

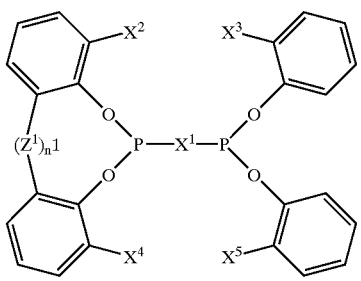

wherein $X^1$ is a bridging group selected from the group consisting of

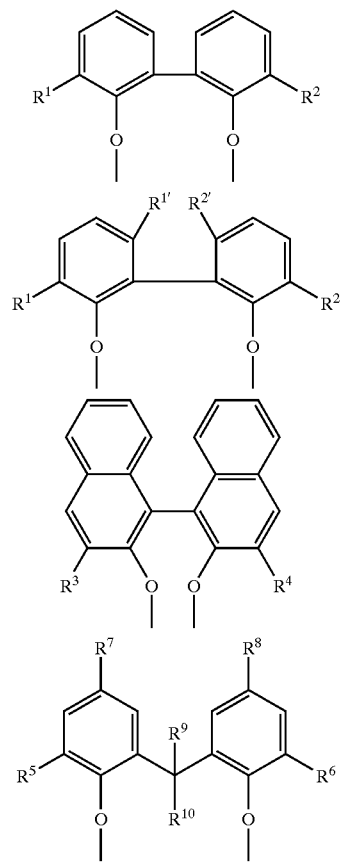

wherein $R^1$, $R^2$, $R^3$, $R^4$, $R^5$, $R^6$, $R^7$, $R^8$, $R^{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR_2^{12}$, acetal, ketal, dialkylamino, or diarylamino, —OR, —$CO_2R^{11}$, —$(CNR^{11})R^{11}$, —$(CNOR^{11})R^{11}$; wherein $R^{11}$ is $C_1$ to $C_{18}$ alkyl, cycloalkyl, aryl, or substituted aryl, —$C(O)R^{12}$, —$C(O)NR^{12}R^{13}$, —O—$C(O)R^{12}$, —$NR^{12}$—$C(O)R^{13}$; wherein $R^{12}$ and $R^{13}$ are independently selected from the group consisting of H, $C_1$ to $C_{18}$ alkyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diamylamino, —$OR^{11}$, —$CO_2R^{11}$, $RCNR^{11}$, or $RCNOR^{11}$; and wherein $R^9$ and $R^{10}$ are independently selected from the group consisting of H, $C_1$ to $C_{18}$ alkyl, cycloalkyl, aryl, or substituted aryl;

wherein $X^2$ through $X^5$ are independently selected from the group consisting of:

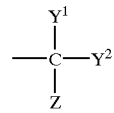

wherein $Y^1$ is independently selected from the group consisting of H, aryl, $CR^{14}_3$, $(CR^{14}_2)n$—$OR^{14}$, and $(CR^{14}_2)n$—$NHR^{15}$; wherein $R^{14}$ is H, $C_1$–$C_{18}$ alkyl, cycloalkyl, or aryl; wherein $R^{15}$ is selected from the group consisting of H, alkyl, cycloalkyl, aryl, —$SO_2R^{11}$, —$SO_2NR^{12}_2$, —$COR^{16}$; wherein $R^{16}$ is H, $C_1$–$C_{18}$ alkyl, cycloalkyl, aryl, or perfluoroalkyl; wherein $Y^2$ is independently selected from the group consisting of aryl, $CR^{14}_3$, $(CR^{14}2)n$—$OR^{14}$, and $(CR^{14}_2)n$—$NHR^{15}$; wherein $R^{14}$ is H, $C_1$–$C_{18}$ alky, cycloalkyl, or aryl; wherein $R^{15}$ is selected from the group consisting of H, alky, cycloalkyl, aryl, —$SO_2R^{11}$, —$SO_2NR^{12}_2$, —$COR^{16}$; wherein $R^{16}$ is H, $C_1$–$C_{18}$ alky, cycloalkyl, aryl, or perfluoroalkyl; wherein Z is selected from the group consisting of $(CR^{14}_2)_n$—$OR^{14}$; wherein n=0–3; and wherein, optionally, either $Y^1$ or $Y^2$ may be linked with Z to form a cyclic ether;

wherein a ligand having the structure of Formula II-A or Formula II-B has at least one aromatic ring carbon in the ortho position to an O bonded to a P bonded through $(Z^1)n^1$ to another aromatic ring carbon in the ortho position to the other O bonded to the P; and wherein $Z^1$ is independently;

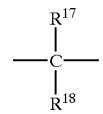

and wherein each $R^{17}$ and $R^{18}$ are independently selected from the group consisting of H, $C_1$ to $C_{18}$ alky, cycloalkyl, aryl, or substituted aryl, and $n^1$ is either one or zero.

11. The process of claim 10 wherein the ligand has either $Y^1$ or $Y^2$ is linked to Z to form a cyclic ether.

12. The process of claim 10 wherein the ligand has the structure of formula II.

13. The process of claim 10 wherein $Y^1$ or $Y^2$ is linked with Z to give the ligand at least one terminal group of the structure of formulae A or B; $Y^3$=O or $CH_2$; and $R^{14}$ is defined as above:

Formula A

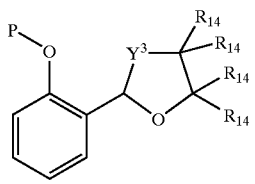

-continued

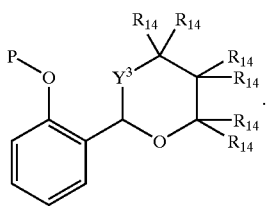

Formula B

14. The process of claim 10 wherein the reactants are in the liquid phase.

15. The process of claim 10 wherein the reactants are in the vapor phase.

16. The process of claim 10 wherein the unsaturated compound is an acyclic, monoethylenically unsaturated compound.

17. The process of claim 10 wherein the unsaturated compound is an acyclic, aromatic olefin compound.

18. The process of claim 16 wherein the acyclic, monoethylenically unsaturated compound has from 2 to 30 carbon atoms.

* * * * *